United States Patent [19]
Tamai et al.

[11] Patent Number: 5,322,962
[45] Date of Patent: Jun. 21, 1994

[54] AROMATIC DIAMINE INTERMEDIATES USEFUL IN THE PREPARATION OF POLYIMIDE

[75] Inventors: Shoji Tamai, Yokohama; Keizaburo Yamaguchi, Chiba; Yuko Ishihara, Kanagawa; Saburo Kawashima, Kanagawa; Hideaki Oikawa, Kanagawa; Toshiyuki Kataoka, Kanagawa; Akihiro Yamaguchi, Kanagawa, all of Japan

[73] Assignee: Mitsui Toatsu Chemicals, Inc., Tokyo, Japan

[21] Appl. No.: 59,758

[22] Filed: May 12, 1993

Related U.S. Application Data

[62] Division of Ser. No. 752,053, Aug. 29, 1991, Pat. No. 5,231,160.

[30] Foreign Application Priority Data

| Sep. 7, 1990 | [JP] | Japan | 2-235841 |
| Sep. 7, 1990 | [JP] | Japan | 2-235842 |
| Dec. 26, 1990 | [JP] | Japan | 2-406781 |
| Dec. 26, 1990 | [JP] | Japan | 2-406786 |
| May 16, 1991 | [JP] | Japan | 3-111443 |

[51] Int. Cl.$^5$ .......................................... C07C 225/22
[52] U.S. Cl. .................................... 564/308; 564/329
[58] Field of Search ......................................... 564/328

[56] References Cited

U.S. PATENT DOCUMENTS

| 3,959,350 | 5/1976 | Rogers | 260/47 C |
| 4,065,345 | 12/1977 | Progar et al. | 156/309 |
| 4,485,140 | 11/1984 | Gannett et al. | 428/260 |
| 4,837,300 | 6/1989 | St. Clair et al. | 528/353 |
| 4,927,736 | 5/1990 | Mueller et al. | 430/275 |
| 4,937,316 | 6/1990 | Ohta et al. | 528/353 |
| 4,959,440 | 9/1990 | Tamai et al. | 528/125 |
| 4,994,544 | 2/1991 | Nagahiro et al. | 528/125 |

FOREIGN PATENT DOCUMENTS 200204 11/1986 European Pat. Off. .
2-18450 1/1990 Japan .

OTHER PUBLICATIONS

Journal of Applied Polymer Science, vol. 26, No. 11, 1981; pp. 3805–3817.
Journal of Chromatography, vol. 119, 1976, pp. 569–579.
Chem. Abstracts, vol. 80, 1974, 82351d.
Chem. Abstracts, vol. 111, 21463q (1989).
Journal of Chromatography, 119 (1976) pp. 569–579.
J. Org. Chem., vol. 40, No. 8, 1975, pp. 1090–1095.

Primary Examiner—Richard L. Raymond
Attorney, Agent, or Firm—Burns, Doane, Swecker & Mathis

[57] ABSTRACT

Disclosed are a novel aromatic diamine; a polymide comprising 1,3-bis(3-aminobenzoyl)benzene or 4,4'-bis(3-aminobenzoyl)biphenyl as a diamine component and having recurring structural units represented by the formula (III):

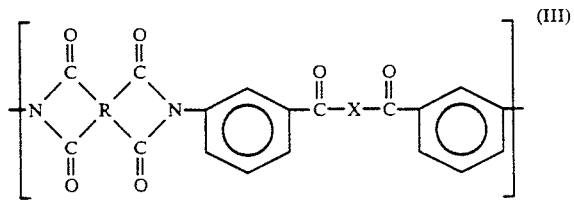

wherein R is a tetravalent radical selected from the group consisting of an aliphatic radical having from 2 to 27 carbon atoms, alicyclic radical, monoaromatic radical, condensed polyaromatic radical, and noncondensed aromatic radical connected each other with a direct bond or a bridge member, and X is a divalent radical of

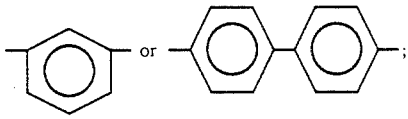

and a polyimide having a terminal aromatic group which is essentially unsubstituted or substituted with a radical having no reactivity with amines or dicarboxylic acid anhydrides or a composition comprising said polyimide.

3 Claims, 4 Drawing Sheets

AROMATIC DIAMINE INTERMEDIATES USEFUL IN THE PREPARATION OF POLYIMIDE

This application is a divisional of application Ser. No. 07/752,053, filed Aug. 29, 1991, now U.S. Pat. No. 5,231,160.

BACKGROUND OF THE INVENTION

1. Field of the Invention

The present invention relates to novel thermoplastic polyimides and a preparation process for these polyimides, aromatic diamines, that is 1,3-bis(3-aminobenzoyl)benzene and 4,4'-bis(3-aminobenzoyl) biphenyl, which are useful as the raw material for polyimide monomer and other chemicals, and a preparation process for these diamines.

1,3-Bis(3-aminobenzoyl)benzene and 4,4'-bis(3-aminobenzoyl) biphenyl are utilized as a raw material for polyimide, polyamide, polyamiderimide, bismaleimide and epoxy resin, and can also be used for the curing agent of maleimide compounds and epoxy compounds. The polyimides of the invention prepared by using these aromatic diamines as the raw material monomer are thermoplastic polyimides having excellent processability.

2. Description of the Prior Art

Polyimide resin has been acknowledged as a material for heat resistant resin. Polyimide is prepared by reacting a diamine compound with tetracarboxylic acid dianhydride, and has excellent mechanical strength, dimensional stability, flame retardance and electrical inventive properties in addition to the high heat-resistance which is the essential property of the resin. On account of such favorable performance, polyimide has been conventionally used in the field of electric and electronic appliances, space and aeronautic equipment, and transportation machinery. Thus, polyimide has been widely used in the fields where heat resistance is required and is expected to be used in other fields in increasing amounts.

Various kinds of polyimide having excellent properties have been developed in order to meet these demands. For example, a most typical polyimide is an aromatic polyimide; Vespel (Trade mark of E. I. Du Pont de Nemours & Co.) which is obtained by reaction of 4, 4'-diaminodiphenyl ether and pyromellitic dianhydride. The polyimide, however, is insoluble and infusible and must be processed by special technique such as sinter molding of powder. Sinter molding is difficult to provide articles having a complex shape and requires finishing operation such as machining in order to obtain satisfactory articles. Thus, sinter molding has a great disadvantage of high processing cost.

Other conventional polyimide resins having excellent properties have no distinct glass transition temperature though excellent in heat resistance, and must be processed by such means as sinter molding in the case of using these resins as molding materials. Other polyimide resins are soluble in solvents such as halogenated hydrocarbons and have disadvantage in solvent resistance, though excellent in processability. Thus previously developed polyimides have both merits and drawbacks in their properties.

New kinds of polyimide which have been improved the above disadvantages or provide with a new performance have been disclosed in order to extend the application field of polyimide.

For example, U.S. Pat. No. 4,065,345 and Japanese Laid-Open Patent HEI 2-018450 have recently disclosed thermoplastic polyimide having recurring units of the following formula (I):

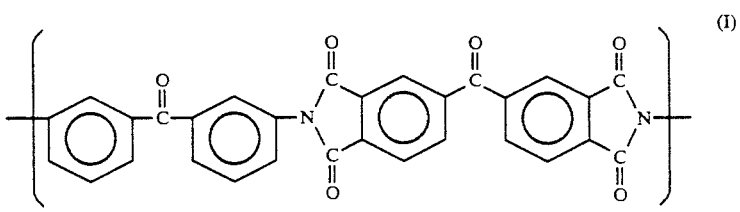

for improving the disadvantages of conventional polyimide. The polyimide is expected for wide use as thermoplastic polyimide having a high glass transition temperature and high elastic modulus.

U.S. Pat. No. 4,485,140 has disclosed polyimide having recurring units of the following formula (II):

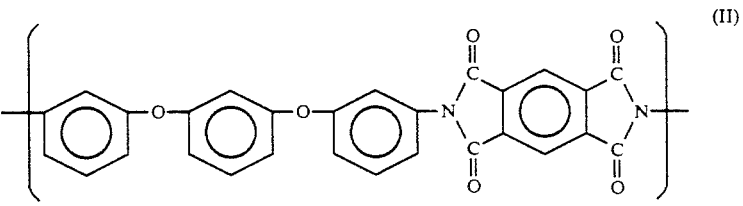

the polyimide has a glass transition temperature of 220° C. and can be melt processable.

However, the polyimide of the latter formula is insufficient in heat resistance, glass transition temperature in particular. The polyimide of the former formula is required to further increase heat-resistance and elastic modulus.

Various methods for improving the diamine component in the raw material monomer have been tried in order to improve properties of polyimide. For example, a polyimide resin having a benzophenone skeleton has been known to have excellent heat-resistance, mechanical properties and adhesive strength. The polyimide resin LARC-TPI which is prepared from 3,3'-diaminobenzophenone has been known to be thermoplastic in addition to having these excellent properties. The resin, however, is still unsatisfactory in processability, although the resin has thermoplastic property.

A method for increasing the molecular chain has recently been employed as a means for enhancing processability.

Known aromatic diamines which can be used for the monomer of polyimide include, for example, 1,3-bis(4-aminobenzoyl)benzene and 1,4-bis[3(or 4)-aminobenzoyl]benzene described in Chemical Abstracts, Vol 80, 82351d; Journal of Chromatography, Vol 119, 569~579 (1976); and Journal of Organic Chemistry, Vol 40, No. 8, 1090~1094 (1975); and 4,4'-bis(4-aminobenzoyl)-biphenyl described in Chemical Abstracts, Vol 111, 214163q; and Mil' to V. 1, Mironov. However, a straight and rigid structure such as 1,4-bis[3(or 4)-aminobenzoyl]benzene and 4,4'-bis(4-aminobenzoyl)-biphenyl is still unsatisfactory for improving the processability of polyimide resin. Consequently, development of polyimide resin having further improved processability and aromatic diamine which can be used for preparing such polyimide resin is strongly demanded.

SUMMARY OF THE INVENTION

One object of the present invention is to provide a thermoplastic polyimide having excellent heat-resistance, processability and chemical resistance, and a process for preparing the polyimide.

Another object of the present invention is to provide a novel aromatic diamine which is useful as a raw material monomer for the above thermoplastic polyimide having excellent properties and also as an intermediate of other various compounds, and a process for preparing the diamine.

As a result of carrying out an intensive investigation in order to accomplish these objects, the present inventors have succeeded in the preparation of 1,3-bis(3-aminobenzoyl)benzene and 4,4'-bis(3-aminobenzoyl)-biphenyl which are position isomers of known 1,3-bis(4-aminobenzoyl)benzene and 4,4'-bis(4-aminobenzoyl)-biphenyl, respectively. They have also found that the polyimide obtained by using the aromatic diamine as a monomer is a thermoplastic polyimide having excellent processability without impairing the essential properties of polyimide.

An aspect of the present invention is a polyimide having recurring structural units of the formula (III):

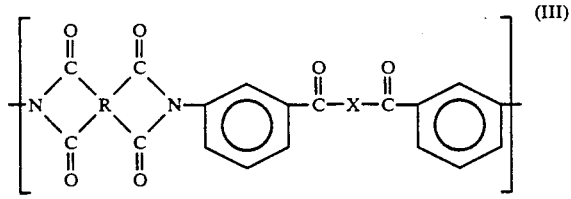

wherein R is a tetravalent radical selected from the group consisting of an aliphatic radical having from 2 to 27 carbon atoms, alicyclic radical, monoaromatic radical, condensed polyaromatic radical, and noncondensed aromatic radical connected to each other with a direct bond or a bridge member, and X is a divalent radical of

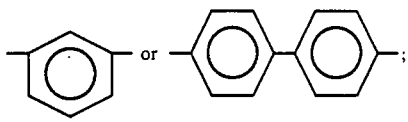

and a process for preparing the polyimide by reacting a diamine component essentially consisting of an aromatic diamine represented by the formula (IV):

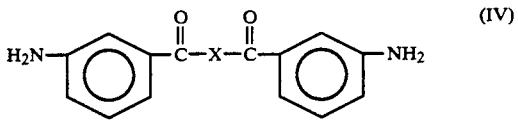

wherein X is a divalent radical of

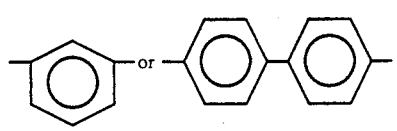

with a tetracarboxylic acid dianhydride represented by the formula (V):

wherein R is a tetravalent radical selected from the group consisting of an aliphatic radical having from 2 to 27 carbon atoms, alicyclic radical, monoaromatic radical, condensed polyaromatic radical and non condensed aromatic radical connected to each other with a direct bound or bridge member, and by thermally or chemically imidizing the resulting polyamic acid.

Another aspect of the present invention is a polyamide having a polymer chain being blocked at the end and having recurring structural units of the formula (III):

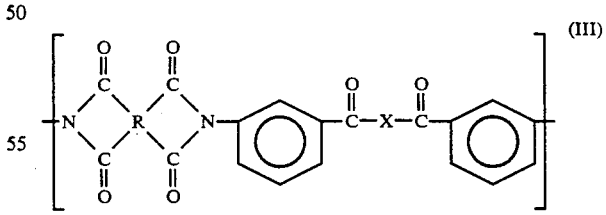

wherein R and X are the same as above, or the polyimide having a terminal aromatic group which is essentially unsubstituted or substituted with a radical having no reactivity with amines or dicarboxylic acid anhydrides, or a composition containing said polyimide; and a process for preparing the polyimide or the composition containing the polyimide by reacting a diamine component essentially consisting of an aromatic diamine represented by the formula (IV):

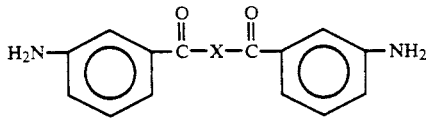

wherein X is the same as above, with a tetracarboxylic acid dianhydride represented by the formula (V):

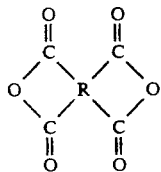

wherein R is the same as above, in the presence of an aromatic dicarboxylic acid anhydride represented by the formula (VI):

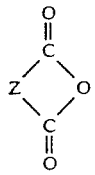

wherein Z is a divalent radical selected from the group consisting of a monoaromatic radical having from 6 to 15 carbon atoms, condensed polyaromatic radical and non-condensed aromatic radical connected to each other with a direct bond or bridge member, or in the presence of an aromatic monoamine represented by the formula (VII):

Z—NH$_2$     (VII)

wherein Z is a divalent radical selected from the group consisting of a monoaromatic radical having from 6 to 15 carbon atoms, condensed polyaromatic radical and non-condensed aromatic radical connected each other with a direct bond or bridge member, and by thermally or chemically imidizing the resulting polyamic acid.

A further aspect of the present invention is a novel aromatic diamine compound represented by the formula (IV):

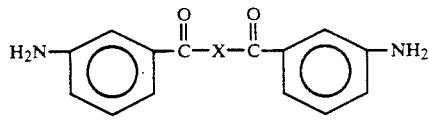

wherein X is

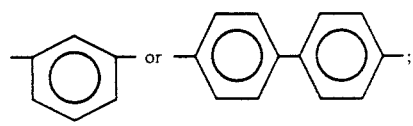

which is useful as a monomer of the polyamide or a raw material of other chemical compounds, that is, 1,3-bis(3-aminobenzoyl)-benzene or 4,4'-bis(3-aminobenzoyl)-biphenyl; a process for preparing 1,3-bis(3-aminobenzoyl)benzene comprising the steps of conducting reducing dehalogenation of 1,3-bis(3-nitro-4-halogenobenzoyl)benzene represented by the formula (VIII):

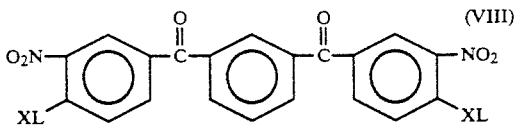

wherein XL is a halogen atom, or comprising the steps of nitrating 1,3-dibenzoylbenzene treating the resultant isomer containing crude 1,3-bis(3-nitrobenzoyl)benzene with alcohol in the presence of an alkaline compound, substantially reacting merely isomers having o-nitro and/or p-nitro groups to convert to the corresponding alkoxy compounds, removing the alkoxy compounds and reducing the resultant 1,3-bis(3-nitrobenzoyl)benzene; and a process for preparing 4,4'-bis(3-aminobenzoyl)biphenyl comprising the step of reacting biphenyl with 3-nitrobenzoyl chloride in the presence of Friedel-Crafts catalyst and reducing the resultant 4,4'-bis(3-nitrobenzoyl)biphenyl having the formula (IX):

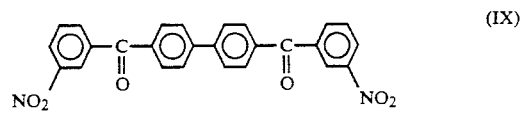

1,3-Bis(3-aminobenzoyl)benzene and 4,4'-bis(3-aminobenzoyl) biphenyl of the invention are novel compounds.

1,3-Bis(3-aminobenzoyl)benzene has three benzene rings connected with two carbonyl groups, and two terminal amino groups are meta located to each carbonyl group.

4,4'-Bis(3-aminobenzoyl)biphenyl has a biphenyl skeleton and carbonyl groups and two terminal amino groups are meta located to the polymer chain.

The aromatic diamines of the invention are novel diamine compounds which are useful as monomers for processable polyimide resin and are very valuable for solving the problems of conventional heat-resistant resin. These aromatic diamines can be prepared from cheap materials with high purity and in good yield. Particularly, the process for preparing 1,3-bis(3-aminobenzoyl)benzene by nitrating 1,3-dibenzoylbenzene, treating the resultant isomer mixture with alcohol in the presence of an alkaline compund, substantially converting merely isomers having o-nitro and/or p-nitro groups to the corresponding alkoxy compounds, removing the alkoxy compounds and reducing the substantially remaining 1,3-bis(3-nitrobenzoyl)benzene, which can be subjected to dehalogenation reaction under mild reducing conditions, can be carried out without formation of alkoxy by products, and can obtain 1,3-bis(3-aminobenzoyl)benzene in high yield without complex purification procedures. Consequently, the process is excellent in industry because production cost is low and the waste causes no environmental pollution.

The polyimide resins prepared from the aromatic diamines of the invention have structural characteristics which makes them excellent in heat-resistance and mechanical properties and have a excellent performance such as processability resulting from the a hooked structure of the polymer molecule and adhesion resulting from the carbonyl group.

DETAILED DESCRIPTION OF THE INVENTION

Figure 1:
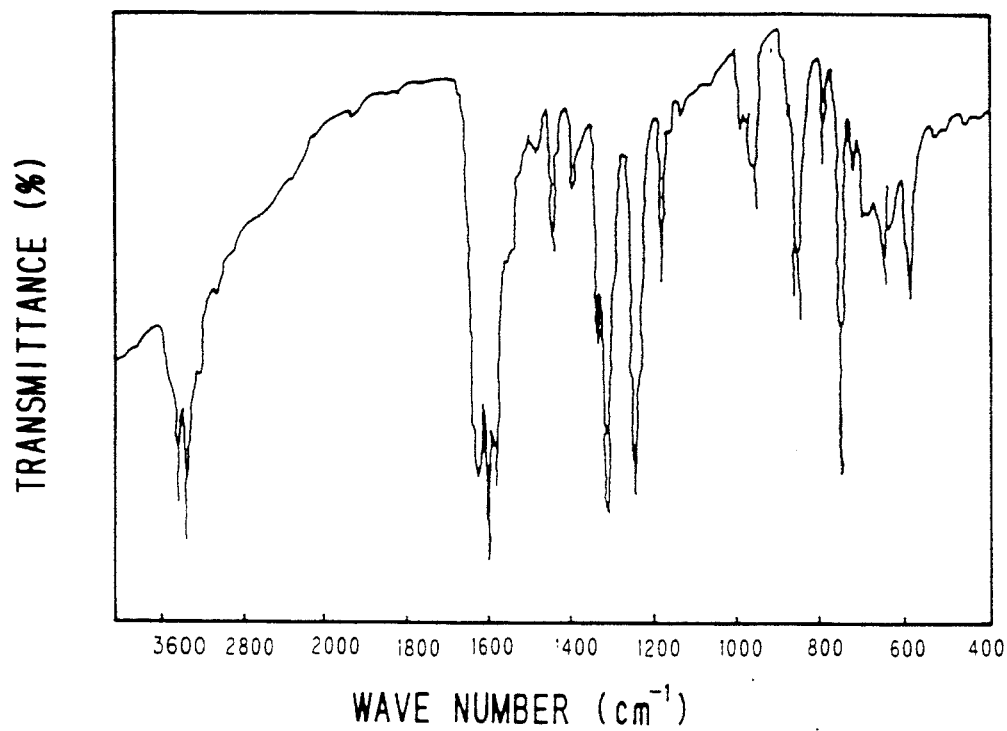
FIG. 1 illustrates an infrared absorption spectrum (KBr tablet method) of 4,4'-bis(3-aminobenzoyl)biphenyl obtained in Example 5.

The polyimide of the invention is essentially a polyimide having recurring structural units of the formula (III):

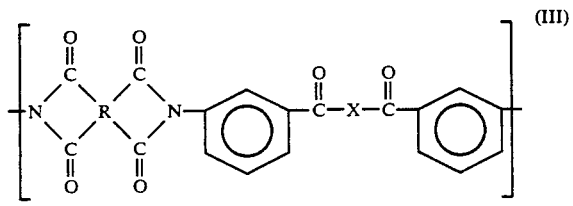

wherein R and X are the same as above, or the polyimide having a terminal aromatic group which is essentially unsubstituted or substituted with a radical having no reactivity with amines or dicarboxylic acid anhydrides, or a composition containing the polyimide.

The polyimide having the recurring structural units can be prepared by using the aromatic diamine of the formula (IV) as the aromatic diamine component that is, 1,3-bis(3-aminobenzoyl)benzene or 4,4'-bis(3-aminobenzoyl)biphenyl, polymerizing the aromatic diamine with one or more aromatic tetracarboxylic dianhydrides of the formula (V), and thermally or chemically conducting dehydration/ring-closure of the resultant polyamic acid.

Consequently, the polyimide of the invention uses the above aromatic diamine, i.e., 1,3-bis(3-aminobenzene of 4,4'-bis(3-aminobenzoyl)biphenyl, as a required monomer. However, other aromatic diamines can also be used as a mixture so long as giving no adverse effect on the good properties of the polyimide.

Other diamines which can be used as a mixture include, for example,
m-phenylenediamine,
o-phenylenediamine,
p-phenylenediamine,
m-aminobenzylamine,
p-aminobenzylamine,
4,4'-diaminodiphenyl ether,
3,3'-diaminodiphenyl ether,
3,4'-diaminodiphenyl ether,
bis(3-aminophenyl) sulfide,
(3-aminophenyl) (4-aminophenyl) sulfide,
bis(4-aminophenyl) sulfide,
bis(3-aminophenyl) sulfoxide,
(3-aminophenyl) (4-aminophenyl) sulfoxide,
bis(4-aminophenyl) sulfoxide,
bis(3-aminophenyl) sulfone,
(3-aminophenyl) (4-aminophenyl) sulfone,
bis(4-aminophenyl) sulfone,
3,3'-diaminobenzophenone,
3,4'-diaminobenzophenone,
4,4'-diaminobenzophenone,
3,3'-diaminodiphenylmethane,
3,4'-diaminodiphenylmethane,
4,4'-diaminodiphenylmethane,
bis [4-(3-aminophenoxy)phenyl] methane,
bis [4-(4-aminophenoxy)phenyl] methane,
1,1-bis [4-(3-aminophenoxy)phenyl] ethane,
1,1-bis [4-(4-aminophenoxy)phenyl] ethane,
1,2-bis [4-(3-aminophenoxy)phenyl] ethane,
1,2-bis [4-(4-aminophenoxy)phenyl] ethane,
2,2-bis [4-(3-aminophenoxy)phenyl] propane,
2,2-bis [4-(4-aminophenoxy)phenyl] propane,
2,2-bis [4-(3-aminophenoxy)phenyl] butane,
2,2-bis [4-(4-aminophenoxy)phenyl] butane,
2,2-bis [4-(3-aminophenoxy)phenyl]-1,1,1,3,3,3-hexafluoropropane,
2,2-bis [4-(4-aminophenoxy)phenyl]-1,1,1,3,3,3-hexafluoropropane,
1,3-bis(3-aminophenoxy)benzene,
1,3-bis(4-aminophenoxy)benzene,
1,4-bis(3-aminophenoxy)benzene,
1,4-bis(4-aminophenoxy)benzene,
4,4'-bis(3-aminophenoxy)biphenyl,
4,4'-bis(4-aminophenoxy)biphenyl,
bis [4-(3-aminophenoxy)phenyl] ketone,
bis [4-(4-aminophenoxy)phenyl] ketone,
bis [4-(3-aminophenoxy)phenyl] sulfide,
bis [4-(4-aminophenoxy)phenyl] sulfide,
bis [4-(3-aminophenoxy)phenyl] sulfoxide,
bis [4-(4-aminophenoxy)phenyl] sulfoxide,
bis [4-(3-aminophenoxy)phenyl] sulfone,
bis [4-(4-aminophenoxy)phenyl] sulfone,
bis [4-(3-aminophenoxy)phenyl] ether,
bis [4-(4-aminophenoxy)phenyl] ether,
1,4-bis [4-(3-aminophenoxy)benzoyl] benzene,
1,3-bis [4-(3-aminophenoxy)benzoyl] benzene,
4,4'-bis [4-(3-aminophenoxy)benzoyl] diphenyl ether,
4,4'-bis [3-(3-aminophenoxy)benzoyl] diphenyl ether,
4,4'-bis [4-(4-amino-α,α-dimethylbenzyl)phenoxy] benzophenone,
4,4'-bis [4-(4-amino-α,α-dimethylbenzyl)phenoxy] diphenyl sulfone,
bis [4-{4-(4-aminophenoxy)phenoxy} phenyl] sulfone,
1,4-bis [4-(4-aminophenoxy)-α,α'-dimethylbenzyl] benzene and
1,3-bis [4-(4-aminophenoxy)-α,α'-dimethylbenzyl] benzene.

These diamines can be used singly or as a mixture.

The tetracarboxylic acid dianhydrides of the formula (V) which can be used in the invention include, for example, ethylenetetracarboxylic dianhydride, cyclopentanetetracarboxylic dianhydride, pyromellitic dianhydride,
3,3',4,4'-benzophenonetetracarboxylic dianhydride,
2,2',3,3'-benzophenonetetracarboxylic dianhydride,
3,3',4,4'-biphenyltetracarboxylic dianhydride,
2,2',3,3'-biphenyltetracarboxylic dianhydride,
2,2-bis(3,4-dicarboxyphenyl)propane dianhydride,
2,2-bis(2,3-dicarboxyphenyl)propane dianhydride,
bis(3,4-dicarboxyphenyl)ether dianhydride,
bis(3,4-dicarboxyphenyl)sulfone dianhydride,
1,1-bis(2,3-dicarboxyphenyl)ethane dianhydride,
bis(2,3-dicarboxyphenyl)methane dianhydride,
bis(3,4-dicarboxyphenyl)methane dianhydride,
2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride,
2,3,6,7-naphthalenetetracarboxylic dianhydride,
1,4,5,8-naphthalenetetracarboxylic dianhydride,
1,2,5,6-naphthalenetetracarboxylic dianhydride,
1,2,3,4-benzenetetracarboxylic dianhydride,
3,4,9,10-perylenetetracarboxylic dianhydride,
2,3,6,7-anthracenetetracarboxylic dianhydride and
1,2,7,8-phenonthrenetetracarboxylic dianhydride.
These dianhydride can be used singly or in combination.

Preferred tetracarboxylic acid dianhydrides are
1,2,4,5-benzenetetracarboxylic dianhydride,
3,3',4,4'-benzophenonetetracarboxylic dianhydride,
2,2',3,3'-benzophenonetetracarboxylic dianhydride,
bis(3,4-dicarboxyphenyl)ether dianhydride,
bis(2,3-dicarboxyphenyl)ether dianhydride,
bis(3,4-dicarboxyphenyl)sulfide dianhydride,
bis(2,3-dicarboxyphenyl)sulfide dianhydride,
bis(3,4-dicarboxyphenyl)sulfone dianhydride,
bis(2,3-dicarboxyphenyl)sulfone dianhydride,
2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane
dianhydride and 1,4-bis(3,4-dicarboxyphenoxy)benzene dianhydride.

In the polyimide and the polyimide containing composition of the invention, the polyimide has recurring structural units represented by the formula (III) and R in the formula (III) is preferably represented by the formula:

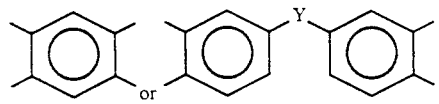

wherein Y is a direct bond, —CO—, —O—, —S—, —SO$_2$—, —CH$_2$—, —C(CH$_3$)$_2$—, —C(CF$_3$)$_2$— or

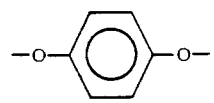

The polyimide of the invention obtained by using the aromatic diamine and the aromatic tetracarboxylic dianhydride as monomer components is a composition essentially consisting of the polyimide having recurring structural units represented by the formula (III), or a polyimide of the formula (III) having a terminal aromatic group which is unsubstituted or substituted with a radical having no reactivity with amines or dicarboxylic acid anhydrides, or a composition containing said polyimide.

The polyimide having, at the end of the polymer chain, the aromatic group which is unsubstituted or substituted with a radical having no reactivity with amines or dicarboxylic acid anhydrides, can be prepared by reacting the above aromatic diamine essentially consisting of 1,3-bis(3-aminobenzoyl)benzene or 4,4'-bis(3-aminobenzoyl)biphenyl with a tetracarboxylic acid dianhydride essentially represented by the formula (V) in the presence of an aromatic dicarboxylic acid anhydride represented by the formula (VI):

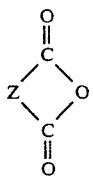 (VI)

wherein Z is the same as above, or an aromatic monoamine represented by the formula (VII):

  Z—NH$_2$ (VII)

wherein Z is the same as above, and by thermally or chemically imidizing the resulting polyamic acid.

Exemplary aromatic dicarboxylic acid anhydrides which can be used in the process include phthalic anhydride,
2,3-benzophenone dicarboxylic anhydride,
3,4-benzophenone dicarboxylic anhydride,
2,3-dicarboxyphenyl phenyl ethane anhydride,
3,4-dicarboxyphenyl phenyl ether anhydride,
2,3-biphenyldicarboxylic anhydride,
3,4-biphenyldicarboxylic anhydride,
2,3-dicarboxyphenyl phenyl sulfone anhydride,
3,4-dicarboxyphenyl phenyl sulfone anhydride,
2,3-dicarboxyphenyl phenyl sulfide anhydride,
3,4-dicarboxyphenyl phenyl sulfide anyhydride,
1,2-naphthalenedicarboxylic anhydride,
2,3-naphthalenedicarboxylic anhydride,
1,8-naphthalenedicarboxylic anhydride,
1,2-anthracenedicarboxylic anhydride,
2,3-anthracenedicarboxylic anhydride and
1,9-anthracenedicarboxylic anhydride.

These aromatic dicarboxylic acid anhydrides may be replaced with a radical having no reactivity with aromatic monoamines or aromatic dicarboxylic acid anhydrides.

Phthalic anhydride is most preferred in these aromatic dicarboxylic acid anhydrides in view of performance of resulting polyimide and practical usage. Excellent processing stability at high temperatures and outstanding chemical resistance in addition to the above good processability make the polyimide very useful as raw material for space- and- air-crafts and electric and electronic appliances.

When phthalic anhydride is used, a portion of the phthalic anhydride may be replaced by other aromatic dicarboxylic acid anhydride as long as imparting no adverse effect on the good properties of the polyimide.

The amount of dicarboxylic acid anhydride used is from 0.001 to 1.0 mole per mole of the aromatic diamine represented by the formula (IV). An amount less than 0.001 mole leads to viscosity increase in high temperature processing and results in poor processability. An amount exceeding 1.0 mole causes lowering of mechanical strengths. Consequently, preferred a amount is from 0.01 to 0.5 mole.

Exemplary aromatic monoamines which can be used in the process include, aniline, o-toluidine, m-toluidine, p-toluidine, 2,3-xylidine, 2,4-xylidine, 2,5-xylidine, 2,6-xylidine, 3,4-xylidine, 3,5-xylidine, o-chloroaniline, m-chloroaniline, p-chloroaniline, o-bromoaniline, m-bromoaniline, p-bromoaniline, o-nitroaniline, m-nitroaniline, p-nitroaniline, o-aminophenol, m-aminophenol, p-aminophenol, o-anisidine, m-anisidine, p-anisidine, o-phenetidine, m-phenetidine, p-phenetidine, o-aminobenzaldehyde, m-aminobenzaldehyde, p-aminobenzaldehyde, o-aminobenzonitrile, m-aminobenzonitrile, p-aminobenzonitrile, 2-aminobiphenyl, 3-aminobiphenyl, 4-aminobiphenyl, 2-aminophenyl phenyl ether, 3-aminophenyl phenyl ether, 4-aminophenyl phenyl ether, 2-aminobenzophenone, 3-aminobenzophenone, 4-aminobenzophenone, 2-aminophenyl phenyl sulfide, 3-aminophenyl phenyl sulfide, 4-aminophenyl phenyl sulfide, 2-aminophenyl phenyl sulfone, 3-aminophenyl phenyl sulfone, 4-aminophenyl phenyl sulfone, α-naphthylamine, β-naphthylamine, 1-amino-2-naphthol, 2-amino-1-naphthol, 4-amino-1-naphthol, 5-amino-1-naphthol, 5-amino-2-naphthol, 7-amino-2-naphthol, 8-amino-1-naphthol, 8-amino-1-naphthol, 8-amino-2-naphthol, 1-aminoanthracene, 2-aminoanthracene and 9-aminoanthracene. These aromatic monoamines may be replaced with a radical having no reactivity with amines or dicarboxylic acid anhydrides.

The amount of aromatic monoamines used is from 0.001 to 1.0 mole per mole of the tetracarboxylic acid dianhydride represented by the formula (V). The amount less than 0.001 mole leads to viscosity increase in processing at high temperature and results in poor processability. An amount exceeding 1.0 mole causes lowering of mechanical strengths. Consequently, a preferred amount is from 0.01 to 0.5 mole.

Thus, in the case of preparing polyimide having a terminal aromatic group which is unsubstituted or substituted with a radical having no reactivity with amines or dicarboxylic acid anhydrides, the mole ratio of the tetracarboxylic acid dianhydride, aromatic diamine and aromatic dicarboxylic acid anhydride or aromatic monoamine is from 0.9 to 1.0 mole of the aromatic diamine and from 0.001 to 1.0 mole of the dicarboxylic acid anhydride or aromatic monoamine per mole of the tetracarboxylic acid dianhydride.

In order to control the molecular weight of formed polyimide in the conventional process, the ratio of tetracarboxylic acid dianhydride to aromatic diamine is usually adjusted. In the process of the invention, the mole ratio of the aromatic diamine to the tetracarboxylic acid dianhydride is from 0.9 to 1.0 in order to obtain polyimide having good melt-flowability.

The polyimide of the invention can be prepared by any process including conventionally known processes. A particularly preferred process is carried out in an organic solvent.

Exemplary organic solvents which can be used include
N,N-dimethylformamide,
N,N-dimethylacetamide,
N,N-diethylacetoamide,
N,N-dimethylmethoxyacetamide,
N-methyl-2-pyrrolidone,
1,3-dimethyl-2-imidazolidinone,
N-methylcaprolactam,
1,2-dimethoxyethane bis (2-methoxyethyl)ether,
1,2-bis(2-methoxyethoxy)ethane,
bis [2-(2-methoxyethoxy)ethyl] ether,
tetrahydrofuran, 1,3-dioxane, 1,4-dioxane, pyridine, picoline, dimethyl sulfoxide, dimethyl sulfone, tetramethylurea, hexamethylphosphoramide, phenol, o-cresol, m-cresol, p-cresol, m-cresylic acid, p-chlorophenol and anisole. These organic solvents can be used singly or as a mixture.

In the practice of the invention, 1,3-bis(3-aminobenzoyl) benzene or 4,4'-bis(3-aminobenzoyl)biphenyl and tetracarboxylic acid dianhydride and aromatic dicarboxylic acid anhydride or aromatic monoamine are added to the organic solvent and the reaction is carried out. Any of the following addition method can be conducted to progress the reaction.

(a) After reacting tetracarboxylic acid dianhydride with 1,3-bis(3-aminobenzoyl)benzene or 4,4'-bis(3-aminobenzoyl)biphenyl, aromatic dicarboxylic acid anhydride or aromatic monoamine is added and the reaction is continued.

(b) After reacting aromatic dicarboxylic acid anhydride with 1,3-bis(3-aminobenzoyl)benzene or 4,4'-bis(3-aminobenzoyl)biphenyl, tetracarboxylic acid dianhydride is added and the reaction is continued.

(c) After reacting tetracarboxylic acid dianhydride with aromatic monoamine, 1,3-bis(3-aminobenzoyl)benzene or 4,4'-bis(3-aminobenzoyl) biphenyl is added and the reaction is continued.

(d) Tetracarboxylic acid dianhydride, and 1,3-bis(3-aminobenzoyl) benzene or 4,4'-bis(3-aminobenzoyl)biphenyl, and aromatic dicarboxylic acid anhydride or aromatic monoamine are added at the same time and successively the reaction is carried out.

The reaction temperature is usually 250° C. or less, preferably 50° C. or less.

No particular restriction is imposed upon the reaction pressure and atmospheric pressure is sufficient to carry out the reaction.

The reaction time differs depending upon the raw material, i.e., 1,3-bis(3-aminobenzoyl)benzene or 4,4'-bis(3-aminobenzoyl)biphenyl, kind of the solvent, and reaction temperature, and is usually from 4 to 24 hours to complete the reaction.

The resulting polyamic acid is further imidized by heating at 100° to 400° C. or chemically imidized by using an imidizing agent such as acetic anhydride to obtain polyimide having recurring structural units corresponding to the polyamic acid.

In an alternative process, 1,3-bis(3-aminobenzoyl)benzene or 4,4'-bis(3-aminobenzoyl)biphenyl and tetracarboxylic acid dianhydride, and additionally aromatic dicarboxylic acid anhydride or aromatic monoamine in the case of forming a terminal aromatic group in the polyimide chain, are dissolved or suspended in the organic solvent and successively heated to carry out formation and imidization of the polyamic acid precursor at the same time. Thus the desired polyimide can also be prepared.

That is, film or powder of the polyimide can be obtained by using conventionally known procedures.

In the melt processing of polyimide of the invention, suitable amounts of other thermoplastic resins can also be blended depending upon the object for use unless impairing the object of the invention. Other thermoplastic resins which can be blended include, for example, polyethylene, polypropylene, polycarbonate, polyarylate, polyamide, polysulfone, polyether sulfone, polyether ketone, polyphenylene sulfide, polyamideimide, polyetherimide and modified polyphenylene oxide.

Fillers which are commonly used for thermoplastic resin composition can also be used as long as giving no adverse effect on the object of the invention. Exemplary fillers include, graphite, carborundum, silica powder, molybdenum disulfide, fluoro resin and other abrasion resistance improvers; glass fibers, carbon fibers, boron fibers, silicon carbide based fibers, carbon whisker, asbestos, metallic fibers, ceramic fibers and other reinforcements; antimony trioxide, magnesium carbonate, calcium carbonate and other flame retardants; clay, mica and other electrical property improvers; asbestos, silica, graphite and other tracking resistance improvers; barium sulfate, silica, calcium metasilicate and other acid resistance improvers; iron powder, zinc powder, aluminum powder, copper powder and other thermal conductivity improvers; and other miscellaneous materials such as glass beads, glass spheres, talc diatomaceous earth, alumina, silicate balloons hydrated alumina, metal oxides and coloring materials.

The aromatic diamine of the invention is particularly useful as a monomer of the above polyimide of the invention, and is a novel aromatic diamine represented by the formula (IV):

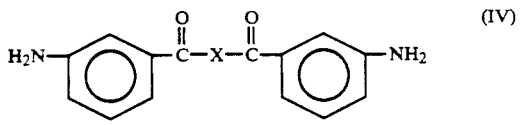

wherein X is

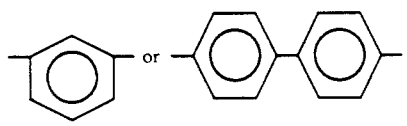

That is, the diamine is 1,3-bis(3-aminobenzoyl)benzene when X

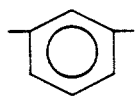

and 4,4'-bis(3-aminobenzoyl)biphenyl when X is

1,3-Bis(3-aminobenzoyl)benzene can be prepared by carrying out reducing dehalogenation of 1,3-bis(3-nitro-4-halogenobenzoyl)benzene represented by the formula (VIII):

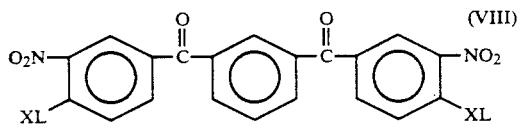

wherein XL is a halogen atom.

The raw material 1,3-bis(3-nitro-4-halogenobenzoyl)benzene is a known compound and can be prepared, for example, by carrying out Friedel-Crafts reaction of isophthaloyl chloride and halogenobenzene and nitrating the resultant 1,3-bis(4-halogenobenzoyl)benzene (Chemical Abstracts, vol 70, 116221x). Preferred halogenobenzene is fluorobenzene, chlorobenzene or bromobenzene.

1,3-Bis(4-halogenobenzoyl)benzene can be nitrated by using mixed acid, fuming nitric acid, nitric acid-acetic acid and other known nitrating agents. Mixed acid or fuming nitric acid is frequently used. The nitrating reaction is carried out by the following procedures.

In the case of nitrating by use of fuming nitric acid, 80~90% nitric acid is used in an amount of from 4 to 12 moles per mole of the raw material. In the case of nitrating by use of mixed acid containing nitric acid or nitrate such as sodium nitrate and potassium nitrate in combination with concentrated sulfuric acid, the mole ratio of nitric acid or nitrate and concentrated sulfuric acid to the raw material is in the range of 1:1.2:1~5. In the nitrating reaction, halogenated hydrocarbon solvents such as methylene chloride, 1,2-dichloroethane, 1,1,2-trichloroethane, chloroform, carbon tetrachloride, 1,1,2,2,-tetrachloroethane and trichloroethylene can be used, if desired.

The nitrating reaction can be carried out by adding the raw material 1,3-bis (4-halogenobenzoyl)benzene to the nitrating agent or by dropwise adding the nitrating agent to the raw material. When the mixed acid is used, previously prepared mixed acid can be used, or the raw material is mixed with one component of the mixed acid and successively the other component can be dropwise added.

Preferred reaction temperature is in the range of from 0° to 80° C. and reaction time is preferably in the range of from 2 to 10 hours. After finishing the reaction, the reaction mixture is discharged into a prescribed amount of ice water. The precipitate formed is filtered to obtain crude 1,3-bis(3-nitro-4-halogenobenzoyl)benzene The crude product can be purified by common methods, if necessary.

The nitro group of 1,3-bis(3-nitro-4-halogenobenzoyl)benzene can be converted to an amino group and halogen atom can be removed at the same time. Alternatively, the nitro group can be converted to the amino group in the first step and the resulting 1,3-bis(3-amino-4-halogenobenzoyl)benzene can be subjected to dehalogenation reaction in the second step.

The preparation of 1,3-bis(3-aminobenzoyl)benzene in one step can utilize common catalytic reduction by noble metal catalysts and reduction by formic acid or formate. The catalyst is preferably a palladium catalyst. The catalyst can be used in the form of metal powder, preferably by adhering on the surface of carriers such as carbon, barium sulfate, silica gel and alumina. The amount of the catalyst used is in the range of from 0.001 to 0.1% by weight as metal for the raw material 1,3-bis(3-nitro-4-halogenobenzoyl)benzene.

Dehydrohalogenating agents are used in the reaction. The dehydrohalogenating agents are hydroxide, carbonate and hydrogen carbonate of alkali metal and alkali earth metal, ammonia or usual organic amines. Exemplary dehydrohalogenating agents which can be used include calcium carbonate, sodium hydroxide, magnesium oxide, ammonium hydrogen carbonate, calcium oxide, lithium hydroxide, barium hydroxide, potassium carbonate, potassium hydroxide, ammonia, triethylamine, tri-n-butylamine, triethanolamine, pyridine and N-methylmorpholine. These dehydrohalogenating agents can be used singly or as a mixture. The amount of the dehydrohalogenating agent used is usually from 0.5 to 5 moles, preferably from 2 to 3 moles per mole of the raw-material 1,3-bis(3-nitro-4-halogenobenzoyl)benzene.

Solvents are usually used in the process. No particular restriction is placed on the solvents as long as the solvents are inert in the reaction. Solvents which can be used include, for example, alcohols such as methanol, ethanol and isopropyl alcohol; glycols such as ethylene glycol and propylene glycol; ethers such as ether, dioxane, tetrahydrofuran, 2-methoxyethanol, ethylene glycol dimethyl ether and diethylene glycol dimethyl ether; aliphatic hydrocarbons such as hexane and cyclohexane; aromatic hydrocarbons such as benzene and toluene; esters such as ethyl acetate and butyl acetate; and aprotic polar solvents such as N,N-dimethylformamide and 1,3-dimethyl-2-imidazolidinone. When progress of the reaction is slow in the presence of a water immiscible solvent, common phase transfer catalysts such as quaternary ammonium salt and quaternary phosphonium salt can be added. The solvent is used in an amount to sufficiently dissolve or disperse the raw material. 1,3-bis(3-nitro-4-halogenobenzoyl)benzene. The amount is usually from 0.5 to 10 times by weight of the raw material.

No particular limitation is placed on the reaction temperature. The reaction temperature is preferably in the range of from 20° to 200° C., more preferably from 20° to 100° C. The reaction pressure usually from atompheric pressure to 50 atm.

In the two step preparation process of 1,3-bis(3-aminobenzoyl)benzene, only the nitro group of the raw material 1,3-bis(3-nitro-4-halogenobenzoyl)benzene is reduced in the first step to obtain 1,3-bis(3-amino-4-halogenobenzoyl)benzene. The reaction can be carried out by common process for reducing nitro groups to amino groups [for example, Jikken Kagaku Koza, vol 15, Oxidation and Reduction (II), published by Maruzen (1977)]. The reduction methods include, for example, reduction by use of iron powder and hydrochloric acid, reduction by sulfides such as sodium sulfide and sodium hydrogen sulfide, reduction by formic acid or formate in the presence of a noble metal catalyst, and catalytic reduction in the presence of a Raney nickel catalyst or a noble metal catalyst having relatively low activity. The catalysts which can be used for the catalytic reduction are common metal catalysts such as nickel, palladium, platinum, rhodium, ruthenium, cobalt and copper.

The progress of reaction in any of the these reduction techniques can be checked by the determination of the theoretical amount of hydrogen absorption, thin layer chromatography or high performance liquid chromatography.

In the second step of the reaction, 1,3-bis(3-amino-4-halogenobenzoyl)benzene obtained in the first step is dehalogenated in the presence of the dehydrohalogenating agent. The reduction and dehalogenating reaction can be carried out under similar conditions to the above one step method.

The reaction mixture obtained by the above reaction methods is hot filtered or extracted to remove the catalyst and inorganic salts, optionally concentrated and 1,3-bis(3-aminobenzoyl)benzene is precipitated in the form of crystals. Alternatively, hydrogen chloride gas is blown through the reaction mixture after removing the catalyst and inorganic salts to isolate hydrochloride of 1,3-bis(3-aminobenzoyl)benzene.

1,3-Bis(3-aminobenzoyl)benzene can also be prepared by another process. 1,3-Dibenzoylbenzene is nitrated to obtain crude 1,3-bis(3-nitrobenzoyl)benzene which contains isomers. The isomer containing crude product is treated with alcohol in the presence of an alkaline compound to substantially react isomers alone which have nitro groups on the o- and/or p-positions. The corresponding alkoxy compounds thus converted are removed. The remaining 1,3-bis(3-nitrobenzoyl)benzene is then reduced.

The process is composed of the step for purifying 1,3-bis(3-nitrobenzoyl)benzene from the crude product obtained by nitrating 1,3-benzoylbenzene, and the step for reducing 1,3-bis(3-nitrobenzoyl)benzene to prepare 1,3-bis(3-aminobenzoyl)benzene (ABB).

1,3-Bis(3-nitrobenzoyl)benzene is purified by the following method. The crude 1,3-bis(3-nitrobenzoyl)benzene raw material is most typically prepared by carrying out Friedel-Crafts reaction of isophthaloyl chloride and benzene and nitrating the resultant 1,3-dibenzoylbenzene. 1,3-Dinitrobenzoylbenzene thus obtained usually contains from 60 to 85% of 1,3-bis(3-nitrobenzoyl)benzene, though different depending upon nitrating conditions, and also contains from 15 to 40% of 1-(2-nitrobenzoyl)-3-(3-nitrobenzoyl)benzene and 1-(3-nitrobenzoyl)-3-(4-nitrobenzoyl)benzene as isomer impurities. Conventionally, there are various problems in order to efficiently obtain the desired 1,3-bis(3-nitrobenzoyl)benzene from such mixture. For example, in order to isolate 1,3-bis(3-nitrobenzoyl)benzene by a recrystallization method, recrystallization with a large amount of solvent must be repeated. Consequently, the yield of 1,3-bis(3-nitrobenzoyl)benzene is greatly decreased, and complex steps and expenses are required for the recovery of recrystallization solvent and disposal of residue.

The present invention relates to a method for effectively separating the isomers with ease.

When the mixture containing 1,3-bis(3-nitrobenzoyl)benzene and the above impurities is treated with alcohol in the presence of the alkaline compound, the nitro groups located substantially at o-positions and p-positions to carbonyl groups are individually converted to corresponding alkoxy groups. Consequently, these isomers can be readily removed from 1,3-bis(3-nitrobenzoyl)benzene and high purity 1,3-bis(3-nitrobenzoyl)benzene can be obtained.

The alcohols which can be used in the method include, for example, lower aliphatic monohydric alcohols such as methanol, ethanol and propanol; alicyclic alcohols such as cyclohexanol; aralkyl alcohols such as benzyl alcohol; and lower polyhydric alcohols such as ethylene glycol. The alcohols are preferably lower aliphatic monohydric alcohols, more preferably aliphatic monohydric alcohols having 5 carbon atoms or less in view of rate of alkoxylation reaction and expenses for alcohol recovery.

No particular limitation is imposed on the amount of the alcohol used as long as the amount is at least equivalent to the sum of isomers contained in the crude 1,3-bis(3-nitrobenzoyl)benzene. However, the alcohol also serves as a solvent and is usually used in an amount which makes stirring possible. Thus, a sufficient amount of the alcohol is from 1 to 5 times by weight for the crude raw material, i.e., 1,3-bis(3-nitrobenzoyl)benzene which contains isomer impurities. Particularly in cases where the same amount or less of alcohol is used, other solvents which are inert to the raw material and alcohol can be added to conduct the reaction. Useful other solvents include, for example, aromatic hydrocarbons such as benzene, toluene and monochlorobenzene; halogenated hydrocarbons such as 1,2-dichloroethane and 1,1,2-trichloroethane; ethers such as dioxane, bis(2-methoxyethyl) ether and tetrahydrofuran; ketones such as acetone and methyl ethyl ketone; aprotic polar solvents such as N,N-dimethylformamide, N-methylpyrrolidone, 1,3-dimethyl-2-imidazolidinone and sulfolane; and water.

Exemplary alkaline compounds which can be used are hydroxide, carbonate, hydrogen carbonate, sulfite and hydrogen sulfite of alkali metals and alkaline earth metals, and include, for example, potassium carbonate, sodium carbonate, potassium hydroxide, sodium hydroxide, calcium hydroxide, sodium sulfite and potassium hydrogen sulfite. Previously prepared alcoholates such as sodium methoxide, sodium ethoxide and potassium butoxide can also be used without any trouble. When the rate of reaction is slow due to the boiling point of lower alcohol solvent, a combination of another high boiling point of solvent with alcoholate of lower alcohol can also be employed for increasing the reaction temperature.

The amount of the alkaline compound is at least a stoichiometrically equal amount, preferably from 1.5 to 5 equivalent weight of the isomers contained in crude 1,3-bis(3-nitrobenzoyl) benzene.

The reaction temperature is selected so as to provide suitable reaction velocity in the reaction system. The reaction is usually carried out at the boiling point of the alcohol used. In order to accelerate the reaction, the reaction can also be conducted at increased temperature under pressure and is practically carried out in the range of 60° to 120° C. The progress of reaction can be checked by thin layer chromatography or high performance liquid chromatography.

Phase transfer catalysts can also be added as catalysts for accelerating the reaction in the process of the invention. Exemplary phase transfer catalysts include quaternary ammonium salts, quaternary phosphonium salts, macrocyclic polyethers such as crown ether, nitrogen containing macrocyclic polyethers such as cryptate, nitrogen containing chain polyethers, polyethylene glycols and polyethylene glycol alkyl ethers.

Purification of 1,3-bis(3-nitrobenzoyl)benzene in the process of the invention is generally carried out by charging crude 1,3-bis(3-nitrobenzoyl)enzene, prescribed amounts of the alkaline compound and alcohol, and optionally the catalyst and other solvent to a reaction vessel, reacting at the boiling temperature of the alcohol or above, cooling the reaction mixture after finishing the reaction, and filtering precipitated 1,3-bis(3-nitrobenzoyl)benzene.

Purified 1,3-bis(3-nitrobenzoyl)benzene thus obtained can be reduced with a common method for reducing nitro groups to amino groups, for example, the method described in Jikken Kagaku Kozo, Vol. 15, Oxidation and Reduction (II), published by Maruzen (1977).

The catalyst, solvent and conditions in the reduction is the same as the above method.

The progress of the reducing reaction is inspected by the determination of the theoretical amount of hydrogen absorption, thin-layer chromatography or high-performance liquid chromatography.

The desired compound of the invention, 1,3-bis(3-aminobenzoyl) benzene can be isolated by hot-filtering or extracting the reaction mixture thus obtained to remove the catalyst and inorganic salt and concentrating the resulting solution, if desired.

4,4'-Bis(3-aminobenzoyl)biphenyl can be prepared by reducing 4,4'-bis(3-nitrobenzoyl)biphenyl having the formula (IX):

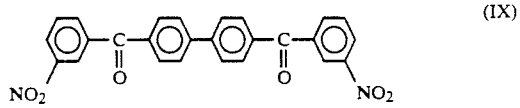
(IX)

The raw material 4,4'-bis(3-nitrobenzoyl)biphenyl can be prepared by Friedel-Crafts reaction of biphenyl and 3-nitrobenzoyl chloride in the presence of a catalyst. In the Friedel-Crafts reaction, 3-nitrobenzoyl chloride is required in an amount of at least 2 moles per mole of biphenyl.

The catalyst which can be used in the reaction are common Friedel-Crafts catalysts. Exemplary catalysts include, anhydrous aluminum chloride, zinc chloride, ferric chloride, antimony pentachloride, titanium tetrachloride, stannic chloride, boron trifluoride and other Lewis acids; and super strong acids such as trifluoromethanesulfonic acid and perfluoroalkanesulfonic acid type ion exchange resin, Nafion-H (Trade mask of E. I. Du Pont de Nemours & Co.). Anhydrous aluminum chloride is particularly preferred.

The amount of the catalyst is required 1 mole or more per mole of the raw material 3-nitrobenzoyl chloride in the case of aluminum chloride catalyst. A little more than 1 mole of the catalyst is usually used. Almost no increase in the effect is found, even though used in an amount of more than 2 moles. Other Lewis acid catalysts and super strong acids such as trifluoromethane sulfonic acid are used in the range of from 0.0005 to 0.1 mole, preferably from 0.001 to 0.05 mole per mole of 3-nitrobenzoyl chloride. No limitation is placed on the amount of super strong acid resin such as Nafion-H and recycled use is also permitted. In a batch reaction, the resin is usually used in the range of from 3 to 200% by weight for the total raw material.

Solvents are usually used in the reaction. Solvents which can be used are inert solvents to the reaction and include, for example, 1,2-dichloroethane, 1,1,2-trichloroethane, 1,1,1-trichloroethane, perchloroethylene, 1,1,2,2-tetrachloroethane, dichlorobenzene and nitrobenzene. No particular limitation is put on the amount of solvents. Solvents are usually used in an amount of from 0.5 to 20 times by weight for the raw material.

When the anhydrous aluminum chloride catalyst is used, the reaction is carried out in a temperature range of from 0° to 120° C. In the case of other catalysts, the reaction is conducted in the range of from 50° to 200° C. The reaction time is in the range of from 1 to 30 hours. The reaction is usually carried out until evolution of hydrogen chloride gas is stopped.

The end point of the reaction can be found by determination of the hydrogen chloride gas evolution or by confirming the consumption of the raw materials, and intermediates with thin-layer chromatography or high-performance liquid chromatography.

Post treatment of the reaction can be carried out by the same procedures as in the case of a common Friedel-Crafts reaction to obtain 4,4'-bis(3-nitrobenzoyl)biphenyl. For example, when anhydrous aluminum chloride is used for the ctalyst, the reaction mixture is poured into a dilute hydrochloric acid to decompose the catalyst and precipitated crystals are isolated by filtration. When the product is dissolved in the solvent, the solvent layer is separated and concentrated or steam-distilled to precipitate the crystals.

4,4'-Bis(3-nitrobenzoyl)biphenyl thus obtained is reduced to 4,4'-bis(3-aminobenzoyl)biphenyl with a common method for reducing nitro groups to amino groups, for example, the method described in Jikken Kagaku Koza, Vol. 15, Oxidation and Reduction (II), published by Maruzen (1977).

However, bis(3-nitrobenzoyl)biphenyl of the invention has two reducible carbonyl groups in addition to nitro groups and it is hence preferred to select suitable conditions for the reduction. Strong reducing conditions are unfavorable because carbonyl groups are reduced to hydroxymethyl groups and further to methylene groups.

Accordingly, it is important to select a method capable of reducing nitro groups alone without reducing carbonyl groups.

Suitable reducing methods include, for example, reduction with iron powder and hydrochloric acid, reduction with sulfides such as sodium sulfide and sodium hydrogen sulfide, reduction with formic acid or formate in the presence of a noble metal catalyst, and catalytic reduction in the presence of a Raney catalyst or a noble metal catalyst having relatively low activity.

Catalytic reduction is advantageous in industry. Useful catalysts for the catalytic reduction are metal catalysts which are commonly used for catalytic reduction and include, for example, nickel, palladium, platinum, rhodium, ruthenium, cobalt and copper. Raney catalysts of nickel, cobalt and copper are preferred. Noble metal catalysts such as palladium, platinum and rhodium have high activity and a portion of carbonyl groups is also reduced simultaneously. Thus, use of the noble metal catalysts as such is unfavorable because selectivity of the desired product is decreased. These catalysts are preferably used after reducing the activity by the addition of, as generally known, a trace amount of a phosphorus or sulfur ingredient.

The amount of the Raney catalysts is in the range of from 1 to 50% by weight, preferably from 3 to 20% by weight for the raw material. Noble metal catalysts are often used that are supported on carriers such as carbon, barium sulfate, silica gel, alumina and cerite in the range of from 0.001 to 10% by weight as metal for the raw material.

No particular restriction is imposed upon the solvents as long as the solvents are inactive in the reaction. Useful solvents include, for example, alcohols such as methanol, ethanol and isopropyl alcohols; glycols such as ethylene glycol and propylene glycol; ethers such as ether, dioxane, tetrahydrofuran, 2-ethoxyethanol and anisole; ketones such as acetone and methyl ethyl ketone; esters such as ethyl acetate and butyl acetate; and aprotic polar solvents such as N,N-dimethylformamide and 1,3-dimethyl-2-imidazolidinone. Aliphatic and aromatic hydrocarbons such as benzene, toluene and cyclohexane can also be used. No particular limitation is placed on the amount of the solvent as long as the solvent can suspend or sufficiently dissolve the raw material. The solvent is usually used in an amount of from 0.5 to 10 times by weight for the raw material.

No particular limitation is imposed upon the reaction temperature. The reaction temperature is generally in the range of from 20° to 200° C., preferably from 20° to 100° C. The reaction pressure is usually from atmospheric pressure to 100 atm. The reaction is generally carried out by dissolving or suspending the raw materials in the solvent, adding the catalyst and introducing hydrogen with stirring at a prescribed temperature to conduct the reduction.

The end point of the reaction can be determined by the determination of amount of hydrogen absorption, thin-layer chromatography or high-performance liquid chromatography.

After finishing the reaction, the reaction mixture is hot-filtered to remove the catalyst. The filtrate is concentrated or diluted if desired, to precipitate the crystal of the desired product.

The crystals thus obtained are filtered and recrystallized, if necessary, to obtain high-purity 4,4'-bis(3-aminobenzoyl)biphenyl.

The present invention will hereinafter be illustrated further in detail by way of examples and comparative examples.

Physical properties in the examples and comparative examples were measured by the following method.

Tg, Tc, Tm: Measured by DSC(Shimadzu DT-40, Series DSC-41M or TMA-41M)

5% weight loss temperature: Measured by DTG(Shimadzu DT-40, Series DTG-40M) in the air Melt viscosity: Measured with Shimadzu-Koka Type Flow Tester CFT 500A under 100 kg load

EXAMPLE 1

To a glass reaction vessel equipped with a thermometer, stirrer and reflux condenser, 240 g (0.54 mole) of 1,3-bis(3-nitro-4-chlorobenzoyl)benzene, 15 g (0.15 mole) of a 36% aqueous hydrochloric acid solution and 470 ml of a 70% aqueous 2-methoxyethanol solution were charged and heated to 70° C. with stirring. Successively, 180 g (3.21 moles) of iron powder was gradually added over an hour while maintaining the internal temperature at 70° to 80° C. Thereafter the reaction mixture was heated to 85° C. and stirred for 8 hours to finish the reaction.

The catalyst was removed by filtration at the same temperature and the filtrate was allowed to cool. The precipitated crystals of 1,3-bis(3-amino-4-chlorobenzoyl)benzene were filtered, washed with a 70% aqueous 2-methoxyethanol solution and dried. Crude crystals of 1,3-bis(3-amino-4-chlorobenzoyl)benzene were thus obtained in the amount of 190 g (95% yield).

The crystals were analyzed by high performance liquid chromatography and determined as having a purity of 88.2% (Area %).

The crude 1,3-bis(3-amino-4-chlorobenzoyl)benzene was recrystallized from 2-methoxyethanol to obtain 256 g of pure 1,3-bis(3-amino-4-chlorobenzoyl)benzene having the purity of 99.4% and a melting point of 208.7°~209.3° C.

In the next step, to a sealed glass reaction vessel equipped with a thermometer, stirrer and reflux condenser, 156 g (0.41 mole) of the above 1,3-bis(3-amino-4-chlorobenzoyl)benzene, 145 g (2.13 mole) of sodium formate, 787 g of 2-methoxyethanol and 43 g of water were charged and heated to 100° C. with stirring. Successively, 7.8 g of a 5% palladium/activated carbon catalyst (a product of M. E. Chemcat Co.) was gradually added and the reaction was continued at 100° C. for 3 hours with stirring. The reaction mixture was cooled to 85° C. and hot filtered to remove the catalyst. The filtrate was poured into 4 l of water. The precipitated yellow crystals were filtered, washed with water and dried. Crude crystal of the desired 1,3-bis(3-aminobenzoyl)benzne were thus obtained in an amount of 126 g (97% yield). The crystals were analyzed by high performance liquid chromatography and determined to have a purity of 85.3%. The crude 1,3-bis(3-aminobenzoyl)benzene was dissolved in 630 g of toluene by heating and hot filtered to remove insoluble matter. Successively, 89 g of a 36% aqueous hydrochloric acid solution was added to the filtrate and allowed to cool. The precipitated crystals of 1,3-bis(3-aminobenzoyl)benzene hydrochloride was recrystallized from ethanol to obtain crystal of pure 1,3-bis(3-aminobenzoyl)benzene hydrochloride. The hydrochloride was dissolved in 1 l of water and neutralized with an aqueous ammonia solution. The precipitated yellow crystals were filtered, washed with water and dried. The desired product, crystals of pure 1,3-bis(3-aminobenzoyl)benzene were thus obtained in an amount of 85 g (67% yield). Melting point was 114.2°~116.9° C.

| Elemental analysis | C | H | N |
| --- | --- | --- | --- |
| Calculated (%) | 75.9 | 5.1 | 8.9 |
| Found (%) | 74.8 | 5.2 | 8.6 |

EXAMPLE 2

To a sealed glass reaction vessel equipped with a thermometer, stirrer and reflux condenser, 5 g (0.011 mole) of 1,3-bis(3-nitro-4-chlorobenzoyl)benzene, 0.2 g of a 5% palladium/activated carbon catalyst (a product of M. E. Chemcat Co.) and 20 ml of isopropyl alcohol were charged and hydrogen was introduced with stirring at 30°~35° C. Absorbed hydrogen was 1.18 l (0.053 mole) over 8 hours. Successively, 2 g (0.033 mole) of a 28% aqueous ammonia solution was added and introduction of hydrogen was continued at 30°~35° C. for 6 hours at 60° C. for 3 hours with stirring. Further absorbed hydrogen was 0.791 g (0.035 mole). The catalyst was removed by filtration at the same temperature, 2.5 g of a 36% aqueous hydrochloric acid solution was added, and the reaction mixture was allowed to cool. The precipitated crystals of 1,3-bis(3-aminobenzoyl)benzene hydrochloride were filtered, dissolved in 100 ml of water, and neutralized with a 28% aqueous ammonia solution. The precipitated yellow crystal of 1,3-bis(3-aminobenzoyl) benzene were filtered, washed with isopropyl alcohol, and dried to obtain 1.3 g of the product (36% yield).

EXAMPLE 3

To a glass reaction vessel equipped with a thermometer, stirrer and reflux condenser, 82.4 g (0.2 mole) of 1,3-bis(3-nitro-4-fluorobenzoyl)benzene, 820 ml of a 80% aqueous ethyl alcohol solution and 82.0 g (1.46 mole) of iron powder were charged, and the mixture was heated to 65° C. with stirring. Successively, a solution containing 6.08 g of 36% hydrochloric acid in 80 ml of 80% ethyl alcohol was added dropwise over 2 hours. The reaction was continued for further an hour with stirring. After finishing the reaction, the mixture was cooled to the room temperature and filtered to remove the iron powder. The filtrate obtained was poured into 2 l of water. The precipitated crystals were filtered, washed with water and dried to obtain 63.5 g of crude crystal of 1,3-bis(3-amino-4-fluorobenzoyl)benzene. The crude crystals weres dispersed in 120 ml of water, 90 g of a 36% aqueous hydrochloric acid solution and 3.8 g of activated carbon were added, and the resulting mixture was heated to dissolve the crude crystals. The resulting mixture was hot filtered. The filtrate was gradually cooled after dissolving 12 g of sodium chloride to precipitate 1,3-bis(3-amino-4-fluorobenzoyl)benzene hydrochloride.

The precipitate was filtered, dissolved in water, and neutralized with a 28% aqueous ammonia solution to obtain 58.4 g of 1,3-bis(3-amino-4-fluorobenzoyl)benzene. The yield was 83.0%. The product had a purity of 99.1% as determined by high performance liquid chromatography.

In the next step, to a sealed glass reaction vessel equipped with a thermometer, stirrer and reflux condenser, 35.2 g (0.1 mole) of the above 1,3-bis(3-aminofluorobenzoyl)benzene, 35.4 g (0.52 mole) of sodium formate, 175 g of 2-methoxyethanol and 9.7 g of water were charged and heated to 100° C. with stirring. Successively, 1.8 g of a 5% palladium/activated carbon catalyst (a product of M. E. Chemcat Co.) was gradually added. Thereafter the reaction mixture was cooled to 85° C., the catalyst was removed by hot filtration and the filtrate obtained was poured into 4 l of water. The precipitated crystals were filtered, washed with water, and dried to obtain 30.7 g of crude crystals of the desired 1,3-bis(3-aminobenzoyl)benzene. The yield was 97.3%. Successively the crude 1,3-bis(3-aminobenzoyl)benzene was dissolved by heating in 150 g of toluene and the insoluble matter was removed by hot filtration. The filtrate was mixed with 22 g of a 36% aqueous hydrochloric acid solution and allowed to cool. The precipitated crystals of 1,3-bis(3-aminobenzoyl) benzene hydrochloride were recrystallized from ethanol to obtain crystals of pure 1,3-bis(3-aminobenzoyl)benzene hydrochloride. The hydrochloride crystals were dissolved in 500 ml of water and neutralized with an aqueous ammonia solution. The precipitated yellow crystals were filtered, washed with water and dried. The desired product obtained, crystals of pure 1,3-bis(3-aminobenzoyl)benzene was obtained in an amount of 19.5 g. The yield was 61%.

EXAMPLE 4

To a sealed glass reaction vessel equipped with a thermometer, stirrer and reflux condenser, 10.7 g (0.02 mole) of 1,3-bis(3-nitro-4-bromobenzoyl)benzene, 0.43 g of a 5% palladium/activated carbon catalyst (a product of M. E. Chemcat Co.) and 50 ml of isopropyl alcohol were charged. Hydrogen was introduced with stirring at 30°~35° C. Absorbed hydrogen was 2.20 l (0.098 mole) over 9 hours. Successively, 3.6 g (0.06 mole) of a 28% aqueous ammonia solution was added and introduction of hydrogen was continued at 30°~35° C. for 6 hours and additionally at 60° C. for 4 hours with stirring. Further absorbed hydrogen was 0.401 g (0.018 mole). The catalyst was removed by filtration at the same temperature, 4.5 g of a 36% aqueous hydrochloric acid solution was added to the filtrate, and the mixture was allowed to cool. The precipitated crystal of 1,3-bis(3-aminobenzoyl)benzene hydrochloride were filtered, dissolved in 200 ml of water, and neutralized with a 28% aqueous ammonia solution. The precipitated crystals were filtered, washed and dried to obtain 1.9 g of 1,3-bis(3-aminobenzoyl)benzene. The yield was 30%.

EXAMPLE 5

To a 2 l reaction vessel equipped with a thermometer and stirrer, 107.9 g (0.7 mole) of biphenyl, 259.8 g (1.4 mole) of 3-nitrobenzoyl chloride, and 1 l of 1,2-dichloroethane were charged and the mixture was heated to 70° C. with stirring. Then 186.2 g (1.4 mole) of anhydrous aluminum chloride was intermittently added over 5 hours while maintainig the reaction temperature in the range of 70°~80° C. and collecting the evolved hydrogen chloride gas into a scrubbing bottle. After finishing the addition, the reaction mixture was aged for 5 hours at the same temperature and cooled to room temperature, and discharged into 2 l of ice water containing 20 g of a 35% aqueous hydrochloric acid solution. After stirring for 30 minutes, the whole mixture was warmed to 60° C. and allowed to stand.

The mixture was separated into two layers. The bottom layer, the 1,2-dichloroethane layer, was collected, washed with 1 l of warm water, concentrated to a half volume, and cooled. A large amount of precipitated crystals were filterted, washed with methanol and dried. The amount of 4,4'-Bis(3-nitrobenzoyl)biphenyl thus obtained was 260.3 g. The yield was 82.2% determined. The purity was 97.5% by high performance liquid chromatography.

Further, 250 g of the crude 4,4'-bis(3-nitrobenzoyl)-biphenyl was dissolved in 2 kg of isobutanol by heating, 13 g of activated carbon was added and thoroughly mixed, and the mixture was hot filtered. The filtrate was allowed to cool. The precipitated large amount of crystals were filtered, washed with methanol and dried. The yield was 220 g. The purity was 99.1% determined by high performance liquid chromatography.

A portion of the recrystallized product was further recrystallized to obtain pure product as light gray crystals. Melting point was 232° C. Following results were obtained by elemental analysis.

| Elemental analysis | C | H | N |
|---|---|---|---|
| Calculated (%) | 69.02 | 3.56 | 6.19 |
| Found (%) | 68.98 | 3.37 | 6.21 |

In the next step, an autoclave was charged with 45.2 g (0.1 mole) of 4,4'-bis(3-nitrobenzoyl)biphenyl which was recrystallized above, 5 g of a Raney nickel catalyst and 300 ml of diethylene glycol dimethyl ether, and thoroughly replaced by nitrogen. Hydrogen was introduced into the autoclave and the pressure was maintained at 50 atmosphere. Temperature of the reaction mixture was increased with vigorous stirring and the reduction was carried out at 70° C. for 5 hours. After finishing the reaction, hydrogen was released, replaced with nitrogen, and the catalyst was removed by filtration.

After heating the filtrate to 90° C., 75 g of a 10% aqueous hydrochloric acid solution was added dropwise and the resulting mixture was gradually cooled. The precipitated crystals of hydrochloride were filtered, washed with water, and recrystallized from 700 ml of a 50% aqueous 2-methoxyethanol solution. The yellow crystals obtained was heat-dissolved in the same recrystallization solvent, neutralized with a dilute aqueous ammonia solution, and gradually cooled. The precipitated yellow crystals were filtered, washed and dried.

The amount of 4,4'-Bis(3-aminobenzoyl)biphenyl thus obtained was 24.4 g (62.2% determined yield). The purity was 99.6% by high performance liquid chromatography. Melting point was 217.3°~218.4° C. Following results were obtained by elemental analysis.

| Elemental analysis | C | H | N |
|---|---|---|---|
| Calculated (%) | 79.52 | 5.14 | 7.14 |
| Found (%) | 79.26 | 5.29 | 7.11 |

Infrared absorption spectrum is illustrated in FIG. 1.

EXAMPLE 6

To a glass reaction vessel, 45.2 g of 4,4'-bis(3-nitrobenzoyl)biphenyl obtained in Example 5, 300 ml of diethylene glycol dimethyl ether, 10 ml of a 35% aqueous hydrochloric acid solution and 10 ml of water were charged, and the mixture was heated to 95°~102° C. with stirring.

The the mixture 90 g of iron powder was intermittently added over 7 hours and aged for 10 hours.

After finishing the reaction, iron powder was removed by filtration. The filtrate was post-treated by the same procedures as Example 1 to obtain 26.6 g of 4,4'-bis(3-aminobenzoyl)biphenyl. The yield was 67.8%.

EXAMPLE 7

To a glass reaction vessel equipped with a thermometer and stirrer, 505 g of 25% fuming sulfuric acid was charged and cooled to 0° C. Successively 113.6 g (0.4 mole) of 1,3-dibenzoylbenzene was gradually added with caution to maintain an internal temperature increase within 10° C. The resulting mixture was cooled to −5° C. with stirring.

A mixture composed of 59.0 g of 94% fuming nitric acid and 63.0 g of 25% fuming sulfuric acid was added dropwise over 6 hours while maintaining the internal temperature in the range of −5° to 5° C. After finishing the dropwise addition, the reaction mixture was further stirred for an hour in the temperature range of −3° to 3° C. After finishing the reaction, the reaction mixture was poured into 2 l of ice water and stirred for an hour. The resulting precipitate was filtered, washed with water, and dried to obtain 146.3 g of crude 1,3-bis(3-nitrobenzoyl)benzene. The yield was 97.8%.

The product had following composition as determined by high-performance liquid chromatography.

| HPLC analysis | |
|---|---|
| 1-(2-Nitrobenzoyl)-3-(3-nitrobenzoyl)benzene | 3.8% |
| 1,3-Bis(3-nitrobenzoyl)benzene | 81.7% |
| 1-(3-Nitrobenzoyl)-3-(4-nitrobenzoyl)benzene | 12.8% |
| Other Compounds | 1.7% |

In the next step, to a glass reaction vessel equipped with a stirrer, reflux condenser and thermometer, 146.3 g (0.39 mole) of crude 1,3-bis(3-nitrobenzoyl)benzene obtained above and 750 g of ethyl alcohol were charged and heated to reflux ethyl alcohol. A solution obtained by previously dissolving 9.8 g of sodium hydroxide in 162.0 g of ethyl alcohol was added dropwise over 8 hours. After finishing addition, the reaction was further continued for 2 hours under reflux. After cooling the reaction mixture, precipitated crystals were filtered, washed and dried to obtain 126.8 g of 1,3-bis(3-nitrobenzoyl)benzene. The yield was 86.7%.

The product had following composition as determined by high-performance liquid chromatography.

| HPLC analysis | |
| --- | --- |
| 1-(2-Nitrobenzoyl)-3-(3-nitrobenzoyl)benzene | 0.1% |
| 1,3-Bis(3-nitrobenzoyl)benzene | 98.1% |
| 1-(3-Nitrobenzoyl)-3-(4-nitrobenzoyl)benzene | 1.4% |
| Other compounds | 0.4% |

In the next step, to a glass reaction vessel equipped with a thermometer and stirrer, 74.8 g (0.2 mole) of 1,3-bis(3-nitrobenzoyl) benzene obtained above, 134 g of iron powder and 680 ml of 70% aqueous 2-methoxyethanol solution were charged and heated to 80° C. Successively, a solution containing 4.2 g of 36% hydrochloric acid in 60 ml of a 70% aqueous 2-methoxyethanol solution was added dropwise over 2 hours at the same temperature. The reaction was further continued for an hour with stirring. After finishing the reaction, the reaction mixture was heated to 95° C. and hot-filtered at the same temperature. The filtrate was poured into 4 l of water. The precipitated crystals were filtered, washed and dried to obtain 59.6 g of 1,3-bis(3-aminobenzoyl)benzene. The yield was 94.3%. The purity was 98.3% (area %) as determined by high-performance liquid chromatography.

In the next step, crude 1,3-bis(3-aminobenzoyl)benzene obtained above was dissolved in a mixture containing 42.6 g of 36% hydrochloric acid in 120 ml of water, treated with activated carbon and allowed to cool. Precipitated 1,3-bis(3-aminobenzoyl)benzene hydrochloride was filtered and dissolved in 500 ml of a 50% aqueous methanol solution and neutralized with a dilute aqueous ammonia solution. Precipitated crystals were filtered washed with water and dried to obtain 56.3 g of pure 1,3-bis(3-aminobenzoyl)benzene. The purity was 99.3% as determined by high-performance liquid chromatography. Melting point was 114.2°~116.9° C.

EXAMPLE 8

To a glass reaction vessel, equipped with a stirrer and thermometer, 170.0 g of 97% sulfuric acid and 56.8 g (0.2 mole) of 1,3-dibenzoylbenzene were charged and cooled to about 0° C. with stirring. At that temperature, 35.2 g of fuming nitric acid having a gravity of 1.52 was added dropwise over 3 hours. After finishing the dropwise addition, the temperature of the reaction mixture was raised to room temperature. Thereafter the reaction mixture was aged for 4 hours to finish the reaction. The resulting reaction mixture was poured into 1.5 l of ice water.

Precipitated crystals were filtered, washed with water and dried to obtain 72.5 g of crude 1,3-bis(3-dinitrobenzoyl)benzene. The yield was 96.9%.

The product had following composition as determined by high-performance liquid chromatography.

| HPLC analysis | |
| --- | --- |
| 1-(2-Nitrobenzoyl)-3-(3-nitrobenzoyl)benzene | 8.8% |
| 1,3-Bis(3-nitrobenzoyl)benzene | 65.1% |
| 1-(3-Nitrobenzoyl)-3-(4-nitrobenzoyl)benzene | 24.8% |
| Other compounds | 1.3% |

To a reaction vessel equipped with a thermometer, stirrer and reflux condenser, 37.4 g (0.1 mole) of crude 1,3-bis(3-nitrobenzoyl)benzene obtained above, 187 g of ethyl alcohol and 3.7 g of polyethylene glycol having a molecular weight of 600 were charged and heated to reflux ethyl alcohol. A solution obtained by previously dissolving 7.5 g of sodium hydroxide in 120 g of ethyl alcohol was added dropwise over 7 hours under reflux. After finishing the reaction, the reaction mixture was cooled. Precipitated crystals were filtered, washed and dried to obtain 24.9 g of 1,3-bis(3-nitrobenzoyl)benzene. The yield was 66.7%.

The product had following composition by high-performance liquid chromatography.

| HPLC analysis | |
| --- | --- |
| 1-(2-Nitrobenzoyl)-3-(3-nitrobenzoyl)benzene | 0.4% |
| 1,3-Bis(3-nitrobenzoyl)benzene | 98.0% |
| 1-(3-Nitrobenzoyl)-3-(4-nitrobenzoyl)benzene | 1.4% |
| Other compounds | 0.2% |

In the next step, 5.6 g (0.015 mole) of the above 1,3-bis(3-nitrobenzoyl)benzene, 0.05 kg of a Raney nickel catalyst and 30 g of ethyl alcohol were charged to an autoclave and reduction was carried out under hydrogen pressure of 20~25 atm at reaction temperature of 50°~60° C. for 3 hours. After finishing reduction, post treatment and purification were carried out by the same procedures as described in Example 1.

1,3-Bis(3-aminobenzoyl)benzene thus obtained had a purity of 99.4% (Area %) as determined by high-performance liquid chromatography.

EXAMPLE 9

To a reaction vessel equipped with a stirrer, reflux condenser and a nitrogen inlet tube, 3.16 g ($1 \times 90^{-2}$ mole) of 1,3-bis(3-aminobenzoyl)benzene and 30.1 g of N,N-dimethylacetamide were charged, and 2,158 g ($9.9 \times 10^{-3}$ mole) of pyromellitic dianhydride was added by portions in a nitrogen atmosphere with caution to prevent temperature increase of the solution. The reaction mixture was stirred for 20 hours at room temperature.

The polyamic acid thus obtained had an inherent viscosity of 1.79 dl/g. The inherent viscosity of the polyamic acid was measured at 35° C. with a solution containing 0.5 g of the polyamic acid in 100 ml of N,N-dimethylacetamide as a solvent.

A portion of the polyamic acid solution was cast on a glass plate and heated at 100° C., 200° C., and 300° C., respectively, for an hour to obtain a polyimide film having a thickness of 50 μm. The polyimide film had a tensile strength of 15.9 kg/mm², tensile elastic modulus of 420 kg/mm² and elongation of 7.3% in accordance with ASTM D-822. The polyimide film had Tg of 274° C.

Figure 2:
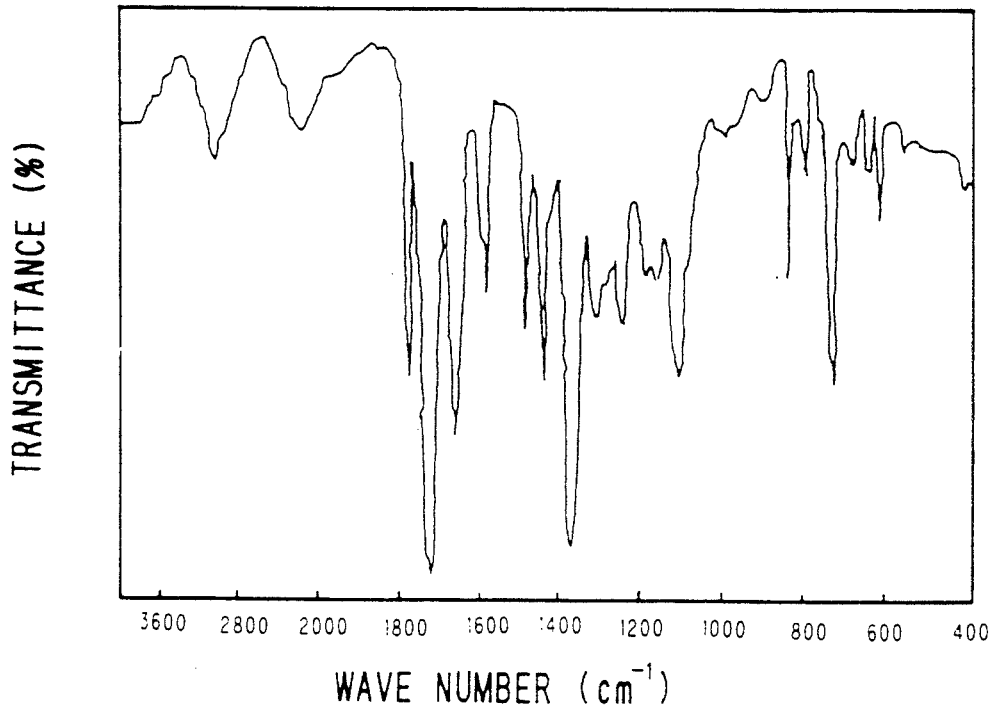
FIGS. 2, 3, 5 and 6 illustrate drawing of infrared absorption spectrum of polyimide powder respectively obtained in Example 9, 10, 19 and 20 of the invention.

An infrared absorption spectrum of the polyimide film is illustrated in FIG. 2. The characteristic absorption band of imide was clearly observed near 1780 cm$^{-1}$ and 1720 cm$^{-1}$ in the spectrum.

COMPARATIVE EXAMPLE 1

A polyamic acid solution was obtained by carrying out the same procedures as described in Example 9 except that 3.16 g ($1 \times 10^{-2}$ mole) of 1,3-bis(3-aminobenzoyl)benzene was replaced by 2.92 g ($1 \times 10^{-2}$ mole) of 1,3-bis(3-aminophenoxy)benzene. The polyamic acid had an inherent viscosity of 1.05 dl/g.

The same procedures as described in Example 9 were carried out by using the polyamic acid solution to obtain a polyimide film. The polyimide film had a tensile strength of 12.8 kg/mm², tensil elastic modulus of 310 kg/mm$^2$, elongation of 9.0% and a glass transition temperature of 202° C.

The polyimide film obtained in Comparative Example 1 had lower glass transition temperature and tensile elastic modulus as compared with the film prepared in Example 9.

COMPARATIVE EXAMPLE 2

A polyamic acid solution was obtained by carrying out the same procedures as described in Example 9 except that 3.16 g (1×10$^{-2}$ mole) of 1,3-bis(3-aminobenzoyl)benzene is replaced by 2.12 g (1×10$^2$ mole) of 3,3-diaminobenzophenone and 2.158 g (9.9×10$^{-3}$ mole) of pyromellitic dianhydride is replaced by 3.188 g (9.9×10$^{-3}$ mole) of 3,3',4,4'-benzophenonetetracarboxylic dianhydride, respectively. The polyamic acid had an inherent viscosity of 1.1 dl/g.

The same procedures as described in Example 9 were carried out by using the polyamic acid solution thus obtained. The resulting polyimide film had a tensile strength of 16.6 kg/mm$^2$, tensile elastic modulus of 360 kg/mm$^2$, elongation of 8.5% and Tg of 2.58° C.

The polyimide film obtained in Comparative Example 2 had lower Tg and tensile elastic modulus as compared with the film prepared in Example 9.

EXAMPLES 10-13

The same procedures as described in Example 9 were carried out by using the tetracarboxylic acid dianhydride as illustrated in Table 1 in an amount as shown in Table 1, respectively.

The polyamic acid solutions thus obtained were cast by the same procedures as described in Example 9 to obtain corresponding polyimide films, respectively.

The inherent viscosity of the polyamic acids, and tensile strength, tensile elastic modulus, elongation and glass transition temperature of the polyimide films are summarized in Table 1 in combination with the results obtained in Example 9.

Figure 3:
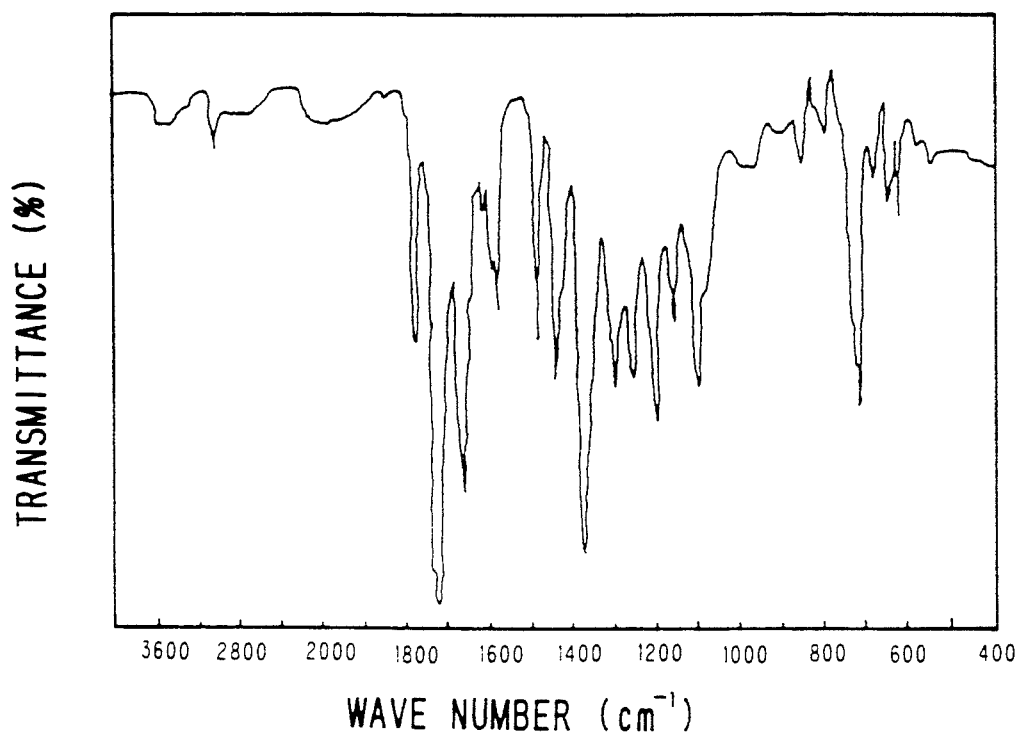

The infrared absorption spectrum of the polyimide film obtained in Example 10 is illustrated in FIG. 3. The characteristic absorption band of imide is clearly observed near 1780 cm$^{-1}$ and 1720 cm$^{-1}$ in the spectrum.

EXAMPLE 14

To a reaction vessel equipped with a stirrer reflux condenser, water separator and a nitrogen inlet tube, 9.48 g (3×10$^{-2}$ mole) of 1,3-bis(3-aminobenzoyl)benzene, 6.213 g (2.85×10$^{-2}$ mole) of pyromellitic dianhydride, 0.444 g (3×10$^{-2}$ mole) of phthalic dianhydride, 0.149 g of γ-picoline, and 62.3 g of m-cresol were charged. The mixture was heated to 145° C. with stirring in a nitrogen atmosphere while distilling out 1 ml of water. The reaction mixture was cooled to the room temperature and poured into 0.5 l of methyl ethyl ketone. The precipitated polyimide powder was filtered, washed with methyl ethyl ketone, and dried at 180° C. 24 hours under reduced pressure to obtain 14.83 g of polyimide powder. The yield was 98.5%.

The polyimide powder thus obtained had an inherent viscosity of 0.54 dl/g. The inherent viscosity was measured at 35° C. with a solution obtained by heat-dissolving 0.50 g of the polyimide powder in 100 ml of a solvent mixture of p-chlorophenol/phenol in a weight ratio of 9/1.

The polyimide powder had a 5% weight loss temperature of 552° C. in the air. The infrared spectrum of the polyimide powder was the same as shown in FIG. 3.

Following results were obtained in the elemental analysis of the polyimide powder.

| Elemental analysis | C | H | N |
|---|---|---|---|
| Calculated (%) | 72.44 | 2.85 | 5.58 |
| Found (%) | 72.64 | 2.74 | 5.56 |

The polyimide powder was insoluble in halogenated hydrocarbon solvents such as methylene chloride and chloroform.

Further, melt viscosity of the polyimide was measured with a KOKA model flow tester under 100 kg load by using an orifice having a diameter of 0.1 mm and a length of 1 cm. The melt viscosity was 5000 poise at 425° C. The strand obtained was red brown, transparent and very flexible.

EXAMPLE 15

The same procedures as described in Example 14 were carried out except that 6.213 g (2.85×10$^{-2}$ mole) of pyromellitic dianhydride was replaced by 9.177 g (2.85×10$^{-2}$ mole) of 3,3',4,4'-benzophenonetetracarboxylic dianhydride. The polyimide powder thus obtained was 17.7 g. The yield was 98%. The polyimide powder had an inherent viscosity of 0.52 dl/g and a 5% weight loss temperature of 549° C. in the air. The infrared absorption spectrum of polyimide powder is the same as shown in FIG. 3. Following results were obtained by the elemental analysis of the polyimide powder.

| Elemental analysis | C | H | N |
|---|---|---|---|
| Calculated (%) | 73.81 | 3.01 | 4.66 |
| Found (%) | 73.59 | 2.97 | 4.72 |

Figure 4:
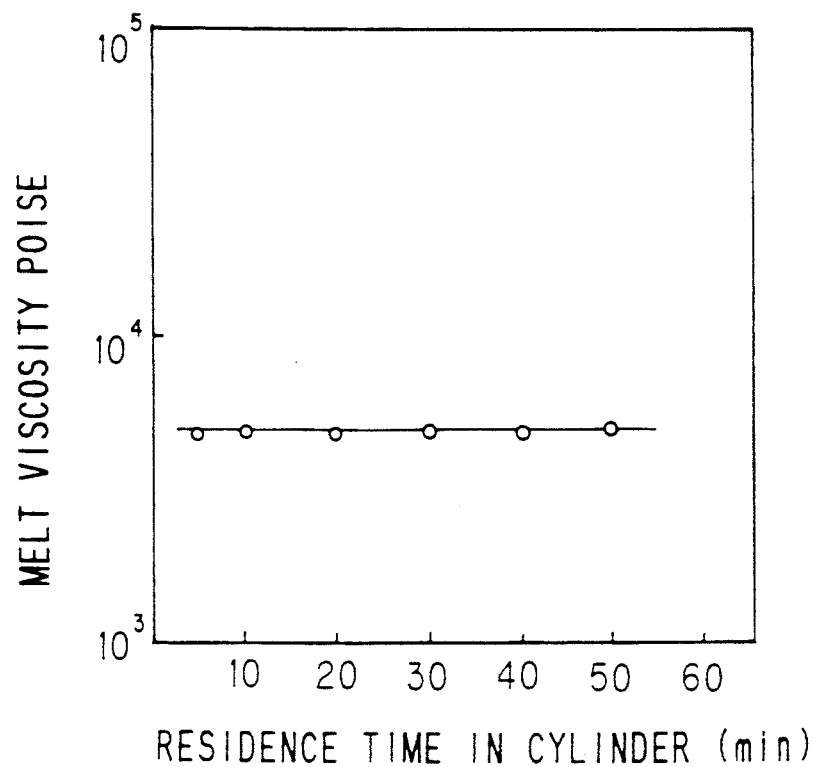
FIGS. 4 and 7 are drawing illustrating the processing stability of polyimide respectively prepared in Examples 15 and 20 of the invention. The processing stability is indicated by melt viscosity variation measured by changing residence time in the cylinder of a flow tester.

The polyimide powder thus obtained had a melt viscosity of 4800 poise at 400° C. The strand obtained was red brown, transparent and very flexible. The processing stability of the polyimide powder was measured by changing the residence time in the cylinder of the flow tester at 400° C. under 100 kg load. Results are illustrated in FIG. 4. The melt viscosity had almost no change, even though residence time in the cylinder was extended. Thus, thermal stability was good.

EXAMPLES 14-16

The same procedures as described in Examples 14 and 15 were carried out by using the tetracarboxylic acid dianhydrides illustrated in Table 2 in amounts shown in Table 2, respectively, to obtain corresponding polyimide powder. The yield, inherent viscosity, 5% weight loss temperature, elemental analysis value, and melt viscosity at 400° C. of the polyimide powder obtained are summarized in Table 2.

EXAMPLE 19

To a reaction vessel equipped with a stirrer, reflux condenser, water separator and a nitrogen inlet tube, 39.2 g (0.1 mole) of 4,4'-bis(3-aminobenzoyl)biphenyl, 20.93 g (0.096 mole) of pyromellitic dianhydride, 1.18 g (8×10$^{-3}$ mole) of phthalic anhydride, 1,4 g of γ-picoline, and 246 g of m-cresol were charged. The mixture was heated to 145° C. with stirring in a nitrogen atmosphere while distilling out 3.5 ml of water. The reaction was further continued at 140°~150° C. for 4 hours. The reaction mixture was cooled to room temperature and poured into 1.5 l of methyl ethyl ketone. The pricipitated polyimide powder was filtered, washed with methyl ethyl ketone, and dried at 180° C. for 24 hours under reduced pressure.

The polyimide powder obtained was 56.92 g. The yield was 98.5%. The polyimide powder had an inherent viscosity of 0.60 dl/g. The inherent viscosity was measured at 35° C. with a solution obtained by heat-dissolving 0.50 g of the polyimide powder in 100 ml of a solvent mixture of p-chlorophenol/phenol in a weight ratio of 9/1.

Figure 5:
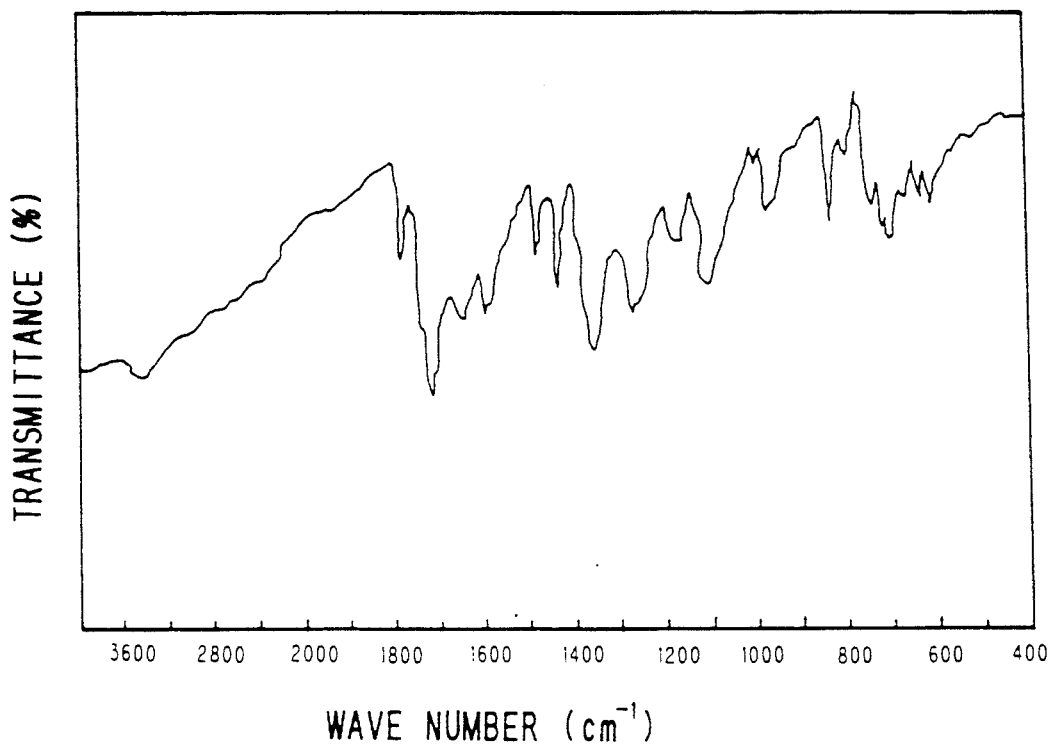

The polyimide powder had a glass transition temperature (Tg) of 284° C., Tc of 370° C., Tn of 454° C., and 5% weight loss temperature of 556° C. The infrared absorption spectrum of the polyimide powder is illustrated in FIG. 5. The characteristic absorption band of imide was clearly observed near 1780 cm$^1$ and 1720 cm$^1$ in the spectrum.

Following results were obtained in the elemental analysis of the polyimide powder.

| Elemental analysis | C | H | N |
|---|---|---|---|
| Calculated (%) | 75.43 | 3.16 | 4.83 |
| Found (%) | 75.39 | 3.12 | 4.84 |

The polyimide powder was insoluble in halogenated hydrocarbon solvents such as methylene chloride and chloroform.

EXAMPLE 20

To the same reaction vessel as used in Example 19, 39.2 g (0.1 mole) of 4,4'-bis(3-aminobenzoyl)biphenyl, 30.59 g (0.095 mole) of 3,3', 4,4'-benzophenonetetracarboxylic dianhydride, 1.48 g (0.01 mole) of phthalic anhydride, 1.4 g of γ-picoline and 285 g of m-cresol were charged. Thereafter the same procedures as described in Example 19 were carried out to obtain 66.45 g of polyimide powder. The yield was 98.2%. The polyimide powder had an inherent viscosity of 0.51 dl/g, glass transition temperature (Tg) of 249° C. and a 5% weight loss temperature of 549° C. in the air.

Figure 6:
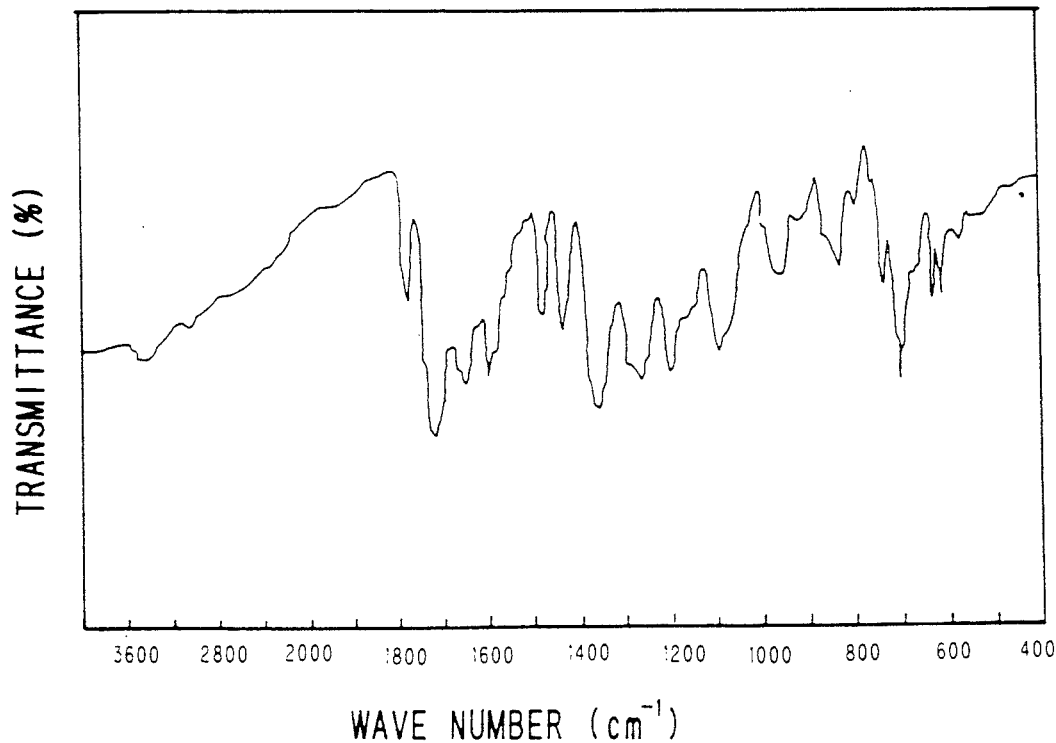

The infrared absorption spectrum of the polyimide powder is illustrated in FIG. 6. The characteristic absorption band of imide is cleary observed near 1780 cm$^1$ and 1720 cm$^1$ in the spectrum.

Following results were obtained in the elemental analysis of the polyimide powder.

| Elemental analysis | C | H | N |
|---|---|---|---|
| Calculated (%) | 76.30 | 3.25 | 4.11 |
| Found (%) | 76.32 | 3.22 | 4.13 |

Figure 7:
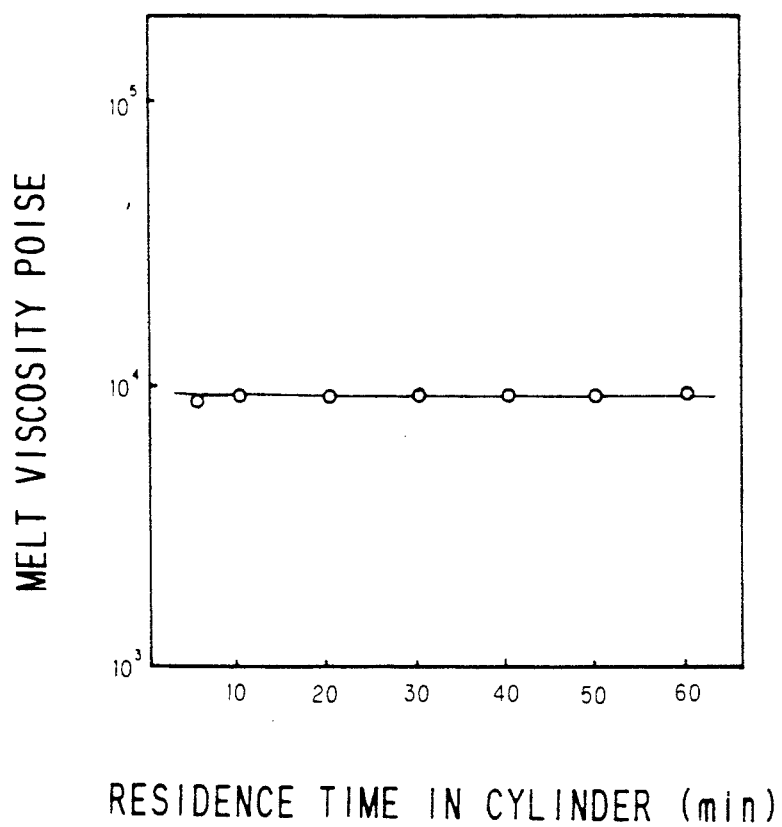

Further, melt viscosity of the polyimide powder was measured with a KOKA model flow tester under 100 kg load by using an orifice having a diameter of 0.1 cm and a length of 1 cm. The melt viscosity was 9000 poise at 380° C. The strand obtained was red brown, transparent and very flexible. The processing stability of the polyimide powder was measured by changing the residence time in the cylinder of the flow tester at 380° C. under 100 kg load. The results are illustrated in FIG. 7. The melt viscosity had almost no change even though the residence time was extended in the cylinder. Thus, heat stability of the polyimide powder was good.

EXAMPLES 21–23

The procedures as described in Examples 19 and 20 were carried out by using the tetracarboxylic acid dianhydrides illustrated in Table 3 in amounts shown in Table 3 to obtain coresponding polyimide powder respectively. The yield inherent viscosity, Tg 5% weight loss temperature and results of elementary analysis are summarized in Table 3.

EXAMPLE 24

To a reaction vessel equipped with a stirrer, reflux condenser and a nitrogen inlet tube, 39.2 g (0.1 mole) of 4,4'-bis(3-aminobenzoyl)biphenyl and 182.3 g of N,N-dimethylacetamide were charged and 21.58 g (0.099 mole) of pyromellitic dianhydride was added by portions in a nitrogen atmosphere with caution to prevent temperature increase of the solution. The resulting mixture was stirred for 20 hours at the room temperature. The polyamic acid thus obtained had an inherent viscosity of 1.20 dl/g.

The inherent viscosity of the polyamic acid was measured at 35° C. with a solution containing 0.5 g of the sample in 100 ml of N,N-dimethylacetamide as a solvent.

A portion of the polyamic acid solution was cast on a glass plate and heated at 100° C., 200° C. and 250° C., respectively, for an hour to obtain a polyimide film having a thickness of 50 μm.

The polyimide film had a tensile strength of 10.3 kg/mm$^2$, tensile elastic modulus of 310 kg/mm$^2$ and elongation of 7.0% in accordance with ASTM D-822. The polyimide film had Tg of 299° C. by TMA penetration method.

EXAMPLES 25–28

The same procedures as described in Example 19 were carried out by using tetracarboxylic acid dianhydrides illustrated in Table 4 in an amounts shown in Table 4 to prepare polyamic acids, respectively. Corresponding polyimide films were prepared from these polyamic acid solutions by carrying out the same procedures as described in Example 19, respectively. The inherent viscosity of the polyamic acid, and tensile strength, tensile elastic modulus and elongation of the resultant polyimide film are summarized in Table 4.

EXAMPLE 29

To the same reaction vessel as used in Example 19, 37.24 g (0.095 mole) of 4,4'-bis(3-aminobenzoyl)biphenyl, 32.2 g (0.1 mole) of 3,3',4,4'-benzophenonetetracarboxylic dianhydride, 0.93 g (0.01 mole) of aniline, 1.4 g of γ-picoline and 285 g of m-cresol were charged. Thereafter the same procedures as described in Example 19 were carried out to obtain 64.5 g of polyimide. The yield was 98%.

The polyimide powder thus obtained had an inherent viscosity of 0.50 dl/g, Tg of 249° C., 5% weight loss temperature of 545° C., and melt viscosity of 3700 poise at 380° C. The strand obtained was red brown, transparent and very flexible.

TABLE 1

| | Diamine compound | tetracarboxylic acid dianhydride | Polyamic acid Inherent viscosity (dl/g) | Polyimide film Glass transition temperature (°C.) | Tensile strength (kg/mm$^2$) | Tensile elastic modulus (kg/mm$^2$) | Elongation (%) |
|---|---|---|---|---|---|---|---|
| Example 9 | 1,3-bis(3-aminobenzoyl)-benzene 3.16 g (1 × 10$^{-2}$ mole) | pyromellitic dianhydride 2.158 g (9.9 × 10$^{-3}$ mole) | 1.79 | 274 | 15.9 | 420 | 7.3 |
| Example 10 | ↑ | 3,3',4,4'-benzophenone-tetracarboxylic dianhydride 3.188 g (9.9 × 10$^{-3}$ mole) | 2.01 | 231 | 14.9 | 430 | 6.1 |
| Example 11 | ↑ | 3,3',4,4'-biphenyl-tetracarboxylic dianhydride 2.911 g (9.9 × 10$^{-3}$ mole) | 1.67 | 257 | 16.0 | 410 | 7.5 |
| Example 12 | ↑ | 3,3',4,4'-diphenylether-tetracarboxylic dianhydride 2.945 g (9.9 × 10$^{-3}$ mole) | 1.80 | 220 | 16.2 | 385 | 8.0 |
| Example 13 | ↑ | 4,4'-(p-phenylene-dioxy)diphthalic dianhydride 3.980 g (9.9 × 10$^{-3}$ mole) | 1.54 | 213 | 19.8 | 360 | 10.5 |

TABLE 2

| | Diamine compound | Tetracarboxylic acid dianhydride | Yield (%) | Inherent viscosity (dl/g) | Td 5.0 *1) (°C.) | Elemental analysis | C | H | N | Melt viscosity 400° C. (poise) |
|---|---|---|---|---|---|---|---|---|---|---|
| Example 16 | 1,3-bis(3-aminobenzoyl)-benzene | 3,3'-4,4'-biphenyltetra-carboxylic dianhydride 8.379 g (2.85 × 10$^{-2}$ mole) | 98.7 | 0.52 | 549 | Calculated (%) Found (%) | 75.83 75.60 | 3.18 3.15 | 4.91 4.87 | 5800 |
| Example 17 | ↑ | 3,3',4,4'-diphenylether-tetracarboxylic dianhydride 8.835 g (2.85 × 10$^{-2}$ mole) | 98.2 | 0.53 | 552 | Calculate (%) Found (%) | 73.31 73.28 | 3.07 3.09 | 4.75 4.78 | 3600 |
| Example 18 | ↑ | 4,4'-(p-phenylene-dioxy)-diphthalic dianhydride 11.45 g (2.85 × 10$^{-2}$ mole) | 98.0 | 0.51 | 557 | Calculated (%) Found (%) | 73.95 73.84 | 3.24 3.27 | 4.14 4.09 | 2400 |

TABLE 3

| | Diamine compound | tetracarboxylic acid dianhydride | yield (%) | Inherent viscosity (dl/g) | Tg (°C.) | Elemental analysis | C | H | N |
|---|---|---|---|---|---|---|---|---|---|
| Example 21 | 4,4'-bis(3-aminobenzoyl)-biphenyl 39.2 g (0.1 mole) | 3,3',4,4'-biphenyl-tetracarboxylic dianhydride 27.93 g (0.095 mole) | 99.0 | 0.55 | 260 | Calculated (%) Found (%) | 77.66 77.69 | 3.38 3.31 | 4.28 4.18 |
| Example 22 | ↑ | 3,3',4,4'-diphenylether- | 98.1 | 0.52 | 225 | Calculated (%) Found (%) | 75.90 75.98 | 3.30 3.26 | 4.18 4.10 |

TABLE 3-continued

| | Diamine compound | tetracarboxylic acid dianhydride | yield (%) | Inherent viscosity (dl/g) | Tg (°C.) | Elemental analysis | | C | H | N |
|---|---|---|---|---|---|---|---|---|---|---|
| Example 23 | ↑ | tetracarboxylic dianhydride 29.45 g (0.095 mole) 4,4'-p-phenylenedyoxi)-diphthalic dianhydride 38.19 g (0.095 mole) | 98.3 | 0.49 | 210 | Calculated (%) Found (%) | | 76.17 76.07 | 3.42 3.39 | 3.70 3.68 |

*1) 5.0% weight loss temperature

TABLE 4

| | Diamine compound | Tetracarboxylic acid dianhydride | Polyimide aciod inherent viscosity (dl/g) | Polyimid film tensile strength (kg/mm²) | Elastic modulus (kg/mm²) | Elongation (%) |
|---|---|---|---|---|---|---|
| Example 25 | 4,4'-bis(3-amino-benzoyl)-biphenyl 39.2 g (0.1 mole) | 3,3',4,4'-benzophenonoe tetracarboxylic dianhydride 31.88 g (0.099 mole) | 1.22 | 11.0 | 325 | 5.5 |
| Example 26 | ↑ | 3,3'-4,4'-biphenyltetra-carboxylic dianhydride 29.11 g (0.099 mole) | 1.30 | 11.5 | 310 | 9.0 |
| Example 27 | ↑ | 3,3',4,4'-diphenylether-tetracarboxylic dianhydride 29.45 g (0.099 mole) | 1.18 | 10.1 | 295 | 11.0 |
| Example 26 | ↑ | 4,4'-(p-phenylenedioxy-diphthalic dianhydride 39.80 g (0.099 mole) | 1.09 | 10.4 | 289 | 15.0 |

What is claimed is:

1. A novel aromatic diamine compound represented by the formula (IV):

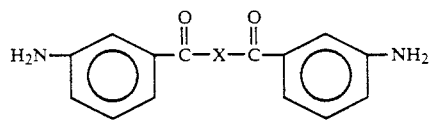

(IV)

wherein X is

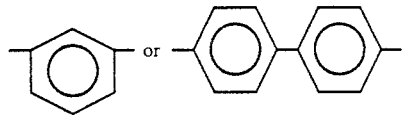

2. 1,3-Bis(3-aminobenzoyl)benzene.
3. 4,4'-Bis(3-aminobenzoyl)biphenyl.